United States Patent
Lee et al.

(10) Patent No.: US 12,403,172 B2
(45) Date of Patent: Sep. 2, 2025

(54) COMPOSITION FOR PREVENTING, ALLEVIATING OR TREATING METABOLIC SYNDROME ACCOMPANIED BY OBESITY AND/OR DIABETES, CONTAINING, AS ACTIVE INGREDIENT, COMPLEX (IB COMPLEX) OF INDIAN GOOSEBERRY EXTRACT AND SPROUT BARLEY EXTRACT

(71) Applicant: HLSCIENCE CO., LTD, Gyeonggi-do (KR)

(72) Inventors: Hae-Yeon Lee, Gyeonggi-do (KR); Jong-Lae Kim, Gyeonggi-do (KR); Tae-Gi Kim, Gyeonggi-do (KR); Mi-Ryeong Park, Gyeonggi-do (KR); Jong-Wook Lee, Seoul (KR); Jin-Seong Yang, Gyeoenggi-do (KR)

(73) Assignee: HLSCIENCE CO., LTD, Gyeonggi-Do (KR)

( * ) Notice: Subject to any disclaimer, the term of this patent is extended or adjusted under 35 U.S.C. 154(b) by 750 days.

(21) Appl. No.: 17/614,749

(22) PCT Filed: May 19, 2020

(86) PCT No.: PCT/KR2020/006545
§ 371 (c)(1),
(2) Date: Nov. 29, 2021

(87) PCT Pub. No.: WO2020/242113
PCT Pub. Date: Dec. 3, 2020

(65) Prior Publication Data
US 2022/0226421 A1    Jul. 21, 2022

(30) Foreign Application Priority Data
May 30, 2019  (KR) .................... 10-2019-0064098

(51) Int. Cl.
*A61K 36/8998*  (2006.01)
*A23L 33/105*  (2016.01)
*A61K 36/185*  (2006.01)
*A61P 3/08*  (2006.01)

(52) U.S. Cl.
CPC ........ *A61K 36/8998* (2013.01); *A23L 33/105* (2016.08); *A61K 36/185* (2013.01); *A61P 3/08* (2018.01)

(58) Field of Classification Search
None
See application file for complete search history.

(56) References Cited

U.S. PATENT DOCUMENTS

2012/0244236 A1    9/2012  Xu
2016/0106793 A1    4/2016  Peltier et al.

FOREIGN PATENT DOCUMENTS

| | | | |
|---|---|---|---|
| CN | 103736071 | * | 1/2014 |
| CN | 105146655 | A | 12/2015 |
| CN | 103736071 | B | 5/2016 |
| CN | 106605822 | A | 5/2017 |
| JP | 2006-008526 | A | 1/2006 |
| JP | 2006-056836 | A | 3/2006 |
| JP | 2006-104094 | A | 4/2006 |
| JP | 2008-050301 | A | 3/2008 |
| JP | 2008-247871 | A | 10/2008 |
| JP | 2010202634 | A | 9/2010 |
| JP | 2011-74051 | A | 4/2011 |
| JP | 2012-121840 | A | 6/2012 |
| JP | 2015-127339 | A | 7/2015 |
| JP | 2016-185931 | A | 10/2016 |
| JP | 2017-105728 | A | 6/2017 |
| KR | 1020140127003 | A | 11/2014 |
| KR | 10-2015-0130128 | A | 11/2015 |
| KR | 1020180003073 | A | 1/2018 |
| KR | 101830048 | B1 | 2/2018 |

OTHER PUBLICATIONS

Bramante et al. (Treatment of Obesity in Patients with Diabetes, Diabetes Spectr Nov. 2017; 30(4):237-243). (Year: 2017).*
International Search Report from corresponding PCT Application No. PCT/KR2020/006545.
Gupta, A. "Dietary interventions and life style modifications on biochemical parameters in type2 diabetes mellitus (Madhumeha)—a clinical study)". Published Jul. 7, 2015.
Fatima, Noor et al. "Ellagic acid in Emblica officinalis exerts anti-diabetic activity through the action on B-cells of pancreas". Published Nov. 20, 2015.
Minaiyan, M. et al. "Effect of *Hordeum vulgare* L. (Barley) on blood glucose levels of normal and STZ-induced diabetic rats". Published Jun. 2014.
Zeng, Y. et al. "Preventative and Therapeutic role of Functional Ingredients of Barley Grass for Chronic Diseases in Human Beings" Published Apr. 4, 2018.
D'Souza, J. et al. "Anti-diabetic effects of the Indian indigenous fruit *Emblica officinalis* Gaertn: active constituents and modes of action" Published Feb. 28, 2014.
Nain, P., et al.; "Antidiabetic and antioxidant potential of Emblica officinalis Gaertn. leaves extract in streptozotocin-induced type-2 diapetes mellitus (T2DM) rats", Journal of Ethonopharmacology, 2012, vol. 142 No. 1, pp. 65-67.

(Continued)

*Primary Examiner* — Melissa S Mercier
(74) *Attorney, Agent, or Firm* — Harness, Dickey & Pierce, P.L.C.

(57) ABSTRACT

The present invention relates to a composition for prevention, improvement or treatment of metabolic syndrome comprising a complex of Indian gooseberry (amla) extract and barley sprout extract as an active ingredient. Specifically, the complex of Indian gooseberry extract and barley sprout extract reduces a body weight, blood sugar, insulin in blood and glycated hemoglobin in blood, and thereby it shows a synergistic effect in improvement of obesity or diabetes, and therefore it can be used as a pharmaceutical composition or health functional food for prevention or treatment of metabolic syndrome such as obesity and diabetes.

7 Claims, 12 Drawing Sheets

(56) References Cited

OTHER PUBLICATIONS

Abstracts of the Annual Meeting of the Japanese Society of Nutrition and Food Science, 2008, vol. 62nd , p. 268, 3F-09a.
Guo Xiaolong, et al., Health Vocational Education, 2012, 30 (20): 88.
Anonymous: "Medoharayogah-2": "Medoharayogah-2", Jan. 1, 2000 (Jan. 1, 2000), India, XP093019030, pp. 1-3.
Byadgi Parameswarappas et al: "Clinical assessment of dietary interventions and lifestyle modifications in Madhumeha (type-2 Diabetes Mellitus)", Ayu (Mumbai), vol. 35, No. 4, Jan. 1, 2014 (Jan. 1, 2014), p. 391.
"Abstracts of The 47th Annual Conference of Research Society for the Study of Diabetes in India" International Journal of Diabetes in Developing Countries, Springer (India) Private Ltd, India, vol. 39, No. Suppl 1, Nov. 1, 2019 (Nov. 1, 2019), pp. 1-42, XP036925362.
Altiok E et al: "Isolation of polyphenols from the extracts of olive leaves (*Olea europaea* L.) by adsorption on silk fibroin", Separation and Purification Technology, Elsevier Science, Amsterdam, NL, vol. 62, No. 2, Sep. 1, 2008 (Sep. 1, 2008), pp. 342-348.
Ahmed Metal: "Phytochemical Screening, Total Phenolic and Flavonoids Contents and Antioxidant Activities of *Citrullus colocynthis* L. and *Cannabis sativa* L.", Applied Ecology and Environmental Research, vol. 17, No. 3, Oct. 8, 2019 (Oct. 8, 2019), pp. 1-19, XP055862116, ISSN: 1589-1623, DOI: 10.15666/aeer/1703_69616979.
Extended European Search Report from corresponding European Patent Application No. 20815311.4, dated Feb. 14, 2023.

\* cited by examiner

COMPOSITION FOR PREVENTING, ALLEVIATING OR TREATING METABOLIC SYNDROME ACCOMPANIED BY OBESITY AND/OR DIABETES, CONTAINING, AS ACTIVE INGREDIENT, COMPLEX (IB COMPLEX) OF INDIAN GOOSEBERRY EXTRACT AND SPROUT BARLEY EXTRACT

CROSS-REFERENCE TO RELATED APPLICATIONS

This application is a national phase application of PCT Application No. PCT/KR2020/006545, filed on 19 May 2020, which claims the benefit and priority to Korean Patent Application No. 10-2019-0064098, filed on 30 May 2019. The entire disclosures of the applications identified in this paragraph are incorporated herein by references.

FIELD

The present application claims the priority based on Korean Patent Application No. 10-2019-0064098 filed on May 30, 2019, and the entire contents disclosed in the description and drawings of the corresponding application are incorporated in the present application.

The present invention relates to a composition for prevention, improvement or treatment of metabolic syndrome comprising natural extract as an active ingredient.

BACKGROUND

Obesity means a condition in which fat is excessively accumulated in the body and may be caused by various causes such as genetic factors, lack of exercise, stress, hormonal imbalance, and westernized diet, and the like. Recently, the prevalence of obesity is increasing every year due to the imbalance of energy intake and consumption, and according to 2017 National Health and Nutrition Survey, the obesity rate in Korea over the age of 19 is 34, 1%, and it is increased 4.9% compared to 29.2% in 2001. Obesity itself may be a health problem, but it is currently recognized as a serious health problem because it is closely related to metabolic syndrome such as hyperlipidemia, hypertension, type 2 diabetes, and hyperglycemia, and the like.

Currently, methods for treating or improving obesity are provided in various ways, and one method is an obesity therapeutic agent. Representative obesity therapeutic agents include appetite suppressants such as Phentermine, Phendimetrazine, Mazindol and the like, and fat absorption inhibitors such as Orlistat, but the appetite suppressants have a problem of side effects such as palpitations, chest pain, dizziness, anxiety and insensibility, and the like, by exciting the central nervous system, and the fat absorption inhibitors have gastrointestinal side effects such as inhibition of fat-soluble vitamin absorption, digestive disorders, and the like.

In addition to drug therapy with these obesity therapeutic agents, dietary therapy to limit energy intake, exercise therapy to increase energy consumption, psychotherapy, behavior therapy, surgical therapy, and the like are also being conducted, but as a preferable method for treatment of obesity, promoting energy consumption through exercise and combining a drug for treating obesity with fewer side effects have been suggested as the safest and most effective method.

Accordingly, it is urgently required to develop a substance for inhibition or treatment of obesity or diabetes, which is safe for the human body and shows an excellent effect. Numerous documents are referred and cited throughout the present specification. The disclosure content of the cited documents is incorporated by reference herein in its entirety and the level of the technical field to which the present invention belongs and the content of the present invention are more clearly described.

The present inventors have tried to develop a natural substance which shows an effect of treatment and inhibition of obesity or diabetes and has no side effects, and as a result, have confirmed that the Indian gooseberry extract and barley sprout extract among various natural raw materials have an excellent therapeutic effect for metabolic syndrome such as obesity or diabetes, and have found the mixing ratio having a synergistic effect for treatment of metabolic syndrome by maximizing the efficacy of each raw material, thereby completing the present invention.

Accordingly, an object of the present invention is to provide the following embodiments.

Embodiment 1. A composition for prevention, improvement or treatment of metabolic syndrome, comprising a complex of Indian gooseberry (*Emblica officinalis*) extract and barley sprout (*Hordeum vulgare*) extract as an active ingredient; or a use of a complex of Indian gooseberry (*Emblica officinalis*) extract and barley sprout (*Hordeum vulgare*) extract for prevention, improvement or treatment of metabolic syndrome, or for preparation of a medicine or a health functional food for prevention, improvement or treatment of metabolic syndrome.

Embodiment 2. The composition or the use according to Embodiment 1, wherein the weight ratio of the Indian gooseberry extract to the barley sprout extract is 4:1~1:1.

Embodiment 3. The composition or the use according to any one of preceding embodiments, wherein the complex of Indian gooseberry extract and barley sprout extract has a synergistic effect compared to each single substance.

Embodiment 4. The composition or the use according to any one of preceding embodiments, wherein the complex of Indian gooseberry extract and barley sprout extract retains the efficacy of fat accumulation inhibition and weight loss, by inhibiting digestion and absorption of fat, and inhibiting fat synthesis and promoting lipolysis, by inhibiting the enzymatic activity of pancreatic lipase; or retains the efficacy of reduction of blood sugar, insulin and glycated hemoglobin, by regulating absorption of blood sugar and promoting glucose metabolism.

Embodiment 5. The composition or the use according to any one of preceding embodiments, wherein the metabolic syndrome is obesity or diabetes.

Embodiment 6. The composition or the use according to any one of preceding embodiments, wherein the Indian gooseberry extract comprises 1 to 5 mg/g of ellagic acid under the condition of acid hydrolysis.

Embodiment 7. The composition or the use according to any one of preceding embodiments, wherein the Indian gooseberry extract comprises 5 to 25 mg/g of ellagic acid under the condition that does not undergo acid hydrolysis.

Embodiment 8. The composition or the use according to any one of preceding embodiments, wherein the barely sprout extract comprises saponarin of 6 to 11 mg/g.

Embodiment 9. The composition or the use according to any one of preceding embodiments, wherein the Indian gooseberry extract or barley sprout extract is squeezed, or extracted using any one selected from the group consisting of water, lower alcohols having 1 to 4 carbon atoms and mixtures thereof as an extraction solvent.

Embodiment 10. The composition or the use according to any one of preceding embodiments, wherein the Indian gooseberry extract or barley sprout extract is dry powder.

Embodiment 11. A pharmaceutical composition or a medicine comprising the composition for prevention, improvement or treatment of metabolic syndrome according to any one of preceding embodiments.

Embodiment 12. A food composition, a health functional food or a food, comprising the composition for prevention, improvement or treatment of metabolic syndrome according to any one of preceding embodiments.

Embodiment 13. A method for preventing, improving or treating metabolic syndrome, comprising administering the composition according to any one of preceding embodiments to a subject having or at risk for having metabolic syndrome.

Embodiment 14. A method for preparation of the composition according to any one of preceding embodiments, comprising
    obtaining Indian gooseberry extract from Indian goose berries including squeezing and drying processes;
    obtaining barley sprout extract from barley sprout including squeezing and drying processes; and
    preparing a complex by mixing the Indian gooseberry extract and barley sprout extract in a weight ratio of 4:1 to 1:1.

Other objects and advantages of the present invention will be more apparent by the following detailed description of the invention, claims and drawings.

Technical Solution

One aspect of the present invention is to provide a composition for prevention, improvement or treatment of metabolic syndrome, comprising a complex of Indian gooseberry (*Emblica officinalis*) extract and barley sprout (*Hordeum vulgare*) extract as an active ingredient.

Indian gooseberry (Phyllanthus emblica L.) is also called *Emblica officinalis* (*Emblica officinalis* Gaertn) or Amla, and has a unique name depending on each region or language. For example, it is also called Amalaki, Emblic Leafflower, Yougan, Anmaroku, Emblic myrobalan, Malaka, Malacca tree, Alonla, Amila, Amilaki, Amila chatra, Nellikai, Nelli, Tasha, Kayruk, Kemurak, Mak Kham pom, and the like. Indian gooseberry is a plant wildly distributed and growing naturally in a wide range of regions such as South Asia including Nepal and Southeast Asia including Malaysia and Central part and South part, and the like. It is cultivated in abundance on the slopes of mountains over 1500 mm above sea level in Taiwan and the Himalayas.

Indian gooseberry is a deciduous tree with a height of 3~8m, and leaves are about 10 mm long and about 2~3 mm wide, and small yellow-green flowers with lemon scent bloom in April~May. Fruits are flat ball-shaped, average 18~25 mm in size, and when ripe, they are light-yellow, shiny, and yellow-green with six pieces of string. The fresh fruit tastes sweet and sour, and bitter, and the aftertaste is sweet. When the fruit is dried, it becomes black, and even if it is dried, nutrients are not weakened, and therefore the dried one is distributed. Amla is also called amalaka, which is considered a sacred tree in Nepal.

Indian gooseberry (Amla) is known to contain vitamin C, minerals, amino acids, tannins, rutin, and the like. Vitamin C of Indian gooseberry is contained 20 times more than orange, and is highly stable against heat, and therefore even if it is exposed to a high temperature for a long time, vitamin is hardly destroyed. The heat-resistance of the vitamin C is considered to be derived from the tannin component contained together, and anti-oxidant, anti-tumor, and anti-inflammatory activity, and the like are shown by these components. In addition, various physiological components such as ellagic acid, gallic acid, quercetin, and the like are comprised in Indian gooseberry (Amla).

Barley sprout (*Hordeum vulgare* L.) refers to a state of young leaves grown by sowing barley seeds in the young order of barley. In one embodiment, barley sprout may be about 10-20 cm young leaves in about 8-15 days after sowing. Barley is one of grains cultivated first in the Eurasian continent about 10,000 years ago, and is known as one of the oldest crops cultivated by mankind. Barley sprout is known as a nutritionally superior food source by having high contents of various kinds of vitamins including vitamin A, vitamin B and vitamin C, and minerals such as calcium, magnesium and potassium, and the like, and containing a large amount of dietary fiber, and therefore the possibility of industrial uses as materials of health functional food and medical supplies is increasing. In the United States, Japan, and the like, young barley leaves are freeze-dried and powdered, thereby being developed and sold as health food, and in Korea, it is commercialized and sold variously as powder, pill, green juice, tea, cosmetics and the like, as general food and health functional food. In aspect of pharmacological activity, the barley sprout shows various functions such as anti-oxidant activity, smooth bowel movements, improvement of cholesterol levels, improvement of blood sugar levels, improvement of hyperlipidemia and an inhibitory effect of obesity, and the like, by various biologically active substances. These biologically active effects are considered to originate from flavonoids including saponarin, lutonarin, and the like.

The composition of the present invention comprises Indian goose beery and barley sprout extracts as active ingredients, and the term 'extract' used herein has a meaning of including extraction results obtained by squeezing or treating an extraction solvent to a raw material, or processed products formulated (for example, powdered).

When the extract used in the composition of the present invention is obtained by treating an extraction solvent to a raw material, various extraction solvents may be used, and for example, a polar solvent or non-polar solvent may be used. As the polar solvent, (i) water, (ii) alcohols (preferably, methanol, ethanol, propanol, butanol, normal-propanol, iso-propanol, normal-butanol, 1-pentanol, 2-butoxyethanol or ethylene glycol), (iii) acetic acid, (iv) DMFO (dimethylformamide) and (v) DMSO (dimethyl sulfoxide), and the like may be used, and as the non-polar solvent, acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride and THE, and the like may be used.

Preferably, the extract used in the present invention may be obtained by squeezing a raw material, or extracting using any one selected from the group consisting of water, lower alcohols having 1 to 4 carbon atoms and mixtures thereof as an extraction solvent, but not limited thereto.

In addition, the term 'extract' used herein has the meaning commonly used as a crude extract in the art as described above, and in a broad sense, includes fractions that the extract is additionally fractionated. In other words, it includes not only extract obtained by squeezing or using the aforementioned extraction solvents, but also one obtained by additionally applying a purification process thereto. For example, fractions obtained by passing the extract through an ultrafiltration membrane having a certain molecular weight cut-off value, and fractions obtained by various purification methods conducted additionally, such as separation by various chromatography (prepared for separation according to size, charge, hydrophobicity or affinity), and the like.

In addition, the extract of the present invention may one that is subjected to an additional process afterwards, for example, one in which a solvent is removed by filtering or performing a concentration or drying process, or one that is subjected to all filtration, concentration and drying. For example, filtration may use filter paper or use a decompression filter, and concentration may use a decompression concentrator, and drying may perform spray drying or freeze-drying, or the like to obtain powdered extract.

According to one embodiment of the present invention, the Indian gooseberry extract prepared as above may comprise 1 to 25 mg/g of ellagic acid, and may comprise 1 to 5 mg/g of ellagic acid under the acid hydrolysis condition depending on the analysis method, and may comprise 5 to 25 mg/g of free ellagic acid of under the condition that does not undergo acid hydrolysis. In addition, the barley sprout extract prepared as above may comprise 6 to 11 mg/g of saponarin.

In the composition of the present invention, the aforementioned Indian gooseberry extract and barley sprout extract may be comprised as a mixture or complex. The mixture or complex may have a synergistic effect compared to each single substance. More specifically, the Indian gooseberry extract and barley sprout extract may be comprised in a weight ratio of 4:1 to 1:1, for example, in a weight ratio of 4:1, 2:1 or 1:1, but not limited thereto.

According to one embodiment, the composition of the present invention may be prepared by one comprising obtaining Indian gooseberry extract from Indian goose berries including squeezing and drying processes; obtaining barley sprout extract from barley sprout including squeezing and drying processes; and preparing a complex by mixing the Indian gooseberry extract and barley sprout extract in a weight ratio of 4:1 to 1:1.

This mixture or complex of the Indian gooseberry extract and barley sprout extract of the present invention retains the efficacy of fat accumulation inhibition and weight loss, by inhibiting digestion and absorption of fat, and inhibiting fat synthesis and promoting lipolysis, by inhibiting the enzymatic activity of pancreatic lipase; or retains the efficacy of reduction of blood sugar, insulin and glycated hemoglobin, by regulating absorption of blood sugar and promoting glucose metabolism, and thereby shows an effect of prevention, improvement or treatment of metabolic syndrome such as obesity or diabetes.

Herein, the term, "pancreatic lipase" is lipase which hydrolyzes triglyceride (TG) that is triglyceride secreted from pancreas into monoglyceride (MG) and fatty acid, and is also called pancreatic triacylglycerol lipase, and is an enzyme which promotes intracellular absorption of triglyceride. Therefore, the pancreatic lipase activity inhibitory ability may be used as an index which evaluates fat absorption in the body.

Herein, the term, "CAMP (Cyclic adenosine monophosphate)" has an increased intercellular concentration by activating adenylate cyclase or inhibiting intercellular CAMP phosphodiesterase action, as B-adrenaline antagonist, prostaglandin E2 (PGE2), and histamines bind to a cell surface receptor. CAMP is involved in promoting triglyceride decomposition and promoting heat generation by activating hormone sensitive lipase (HSL) that is lipase. Therefore, the CAMP level may be used as an index for evaluating lipolysis.

Herein, the term, "Glycerol release" indicates the amount of glycerol released, and is divided into glycerol and fatty acid when triglyceride (TG) present in fat globules accumulated in an adipocyte. Therefore, the content of free glycerol may be used as an index for evaluating decomposition of triglyceride (TG) in fat globules.

Herein, the term, "IRS (Insulin receptor substrate)" is an insulin receptor substrate distributed in systemic tissue such as muscle, liver, fat tissue, and the like, and is involved in the insulin signaling pathway to perform a function of regulating sugar and lipid metabolism.

Herein, the term, "PI3K (Phosphoinositide 3-Kinase)" is phosphorylate which is involved in the insulin signaling pathway, and interacts with the insulin receptor substrate, "IRS (Insulin receptor substrate)", to function to regulate blood sugar absorption and inhibit fat synthesis.

Herein, the term, "GLUT4 (glucose transporter 4)" is a glucose receptor mostly present in a adipocyte and a muscle cell, and becomes an index for inhibiting fat synthesis from glucose metabolism by transferring glucose into the cell membrane from the cell dependently on insulin. When insulin resistance by fat accumulation occurs, GLUT4 translocation does not occur smoothly, and the increase of GLUT4 expression performs a function to regulate glucose metabolism in the body by transferring glucose to the inside of the cell and using it as energy.

Furthermore, the present invention provides a pharmaceutical composition for prevention and treatment of metabolic syndrome such as obesity or diabetes, formulated as a pharmaceutical unit dosage form, by comprising the composition containing the active ingredient, and adding a pharmaceutically acceptable carrier, excipient or diluent, or the like.

Herein, the pharmaceutically acceptable carrier is commonly used for formulation, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, propyl hydroxybenzoate, talc, magnesium stearate and mineral oil, and the like, but not limited thereto.

In addition, when the composition comprising the active ingredient is formulated, it may be prepared using a commonly used diluent or excipient such as a filler, an extender, a binder, a wetting agent, a disintegrating agent, a surfactant, and the like.

Moreover, the pharmaceutical dosage form may be used by formulating into a form of oral formulations such as powder, granules, tablets, capsules, suspension, emulsion, syrup, aerosol, and the like, external preparations, suppositories and sterile injection solutions.

The solid preparation for oral administration may be prepared by mixing at least one of excipients to the extract or powder, and for example, starch may be prepared by mixing calcium carbonate, sucrose or lactose, gelatin, and the like. In addition, other than the simple excipient, lubricants such as magnesium stearate and talc may be used.

In the formulation for parenteral administration, sterile aqueous solution, a non-aqueous solvent, suspension, an emulsion, a freeze-dried formulation, and suppositories may be comprised.

As the non-aqueous solvent and suspension, plant oil such as propylene glycol, polyethylene glycol, and olive oil, and ester injectable with ethyl oleate, and the like may be used.

As a base compound of suppositories, witepsol, macrogol, tween 61, cacao butter, laurin butter, glycerogelatin, and the like may be used. In addition, lubricants such as magnesium stearate and talc may be used.

The pharmaceutical composition of the present invention may be orally administered or parenterally administered (for example, applied intravenously, subcutaneously, intraperitoneally or locally) depending on the desired method, and the dosage varies depending on the patient's condition and body weight, the degree of disease, age, gender, drug form, administration route and period, but it may be appropriately selected by those skilled in the art.

In addition, the present invention provides a health functional food composition for prevention or improvement of metabolic syndrome such as obesity or diabetes formulated into health functional food by comprising the composition containing the active ingredient and adding a food supplement additive.

Herein, the food capable of adding the extract includes for example, various kinds of food, beverages, gum, tea, vitamin complexes, health functional food, and the like. The health functional food composition of the present invention does not have a particular limitation on other components except for containing the extract and it may contain various flavoring agents or natural carbohydrates, or the like, such as common food and beverages, as an additional component.

In the natural carbohydrates, common saccharides such as monosaccharides, for example, glucose, fructose; disaccharides, for example, maltose, sucrose; polysaccharides, for example, dextrin, cyclodextrin, and the like, and sugar-alcohols such as xylitol, sorbitol, erythritol, and the like may be present.

In addition thereto, as the flavoring agent, natural flavoring agents (thaumatin, stevia extract (for example, rebaudioside A, glycyrrhizin, etc.) and synthetic flavoring agents (saccharin, aspartame, etc.) may be advantageously used.

In addition thereto, the extract, powder or complex of the present invention may contain various nutrients, vitamins, minerals (electrolytes), flavoring agents such as synthetic flavoring agents and natural flavoring agents, coloring agents and enhancers, pectic acid and its salt, organic acids, protective colloid thickeners, pH adjusting agents, stabilizers, preservatives, glycerin, alcohols, carbonizing agents used for carbonated beverages, and the like.

Besides, the extract, powder or complex of the present invention may contain flesh for preparation of natural fruit juice and vegetable beverages. This component may be used independently or in combination.

Advantageous Effects

The complex composed of the Indian gooseberry extract and barley sprout extract of the present invention exhibits the efficacy of inhibiting digestion and absorption of fat, and more specifically, it exhibits the efficacy of inhibiting digestion and absorption and promotes GLUT4 signaling including IRS and PI3K and thereby inhibits fat synthesis from glucose metabolism, and promotes lipolysis through regulation of cAMP expression and thereby increases the amount of glycerol released outside cells to inhibit fat accumulation, and regulates absorption of blood sugar and promotes glucose metabolism and thereby reduces a body weight, blood sugar, insulin and glycated hemoglobin, and thereby it retains excellent efficacy of prevention, improvement or treatment of metabolic syndrome such as obesity or diabetes.

In addition, the Indian gooseberry extract and barley sprout extract of the present invention is a complex composed of natural extracts which are non-toxic, have no side effects, and are harmless to the human body, and may be usefully used for effective prevention, improvement or treatment of metabolic syndrome

DETAILED DESCRIPTION

Figure 1:
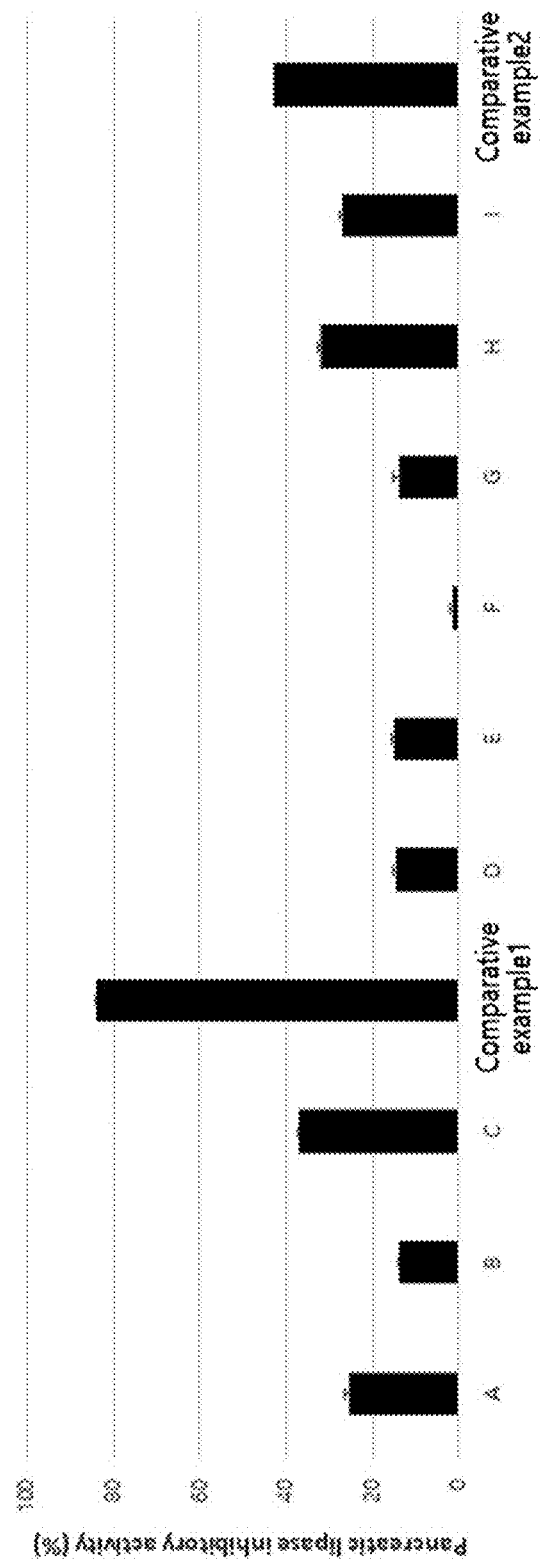
FIG. 1 is a drawing which shows the pancreatic lipase inhibitory activity for 11 kinds of natural substances including Indian gooseberry extract and barley sprout extract.
Figure 2:
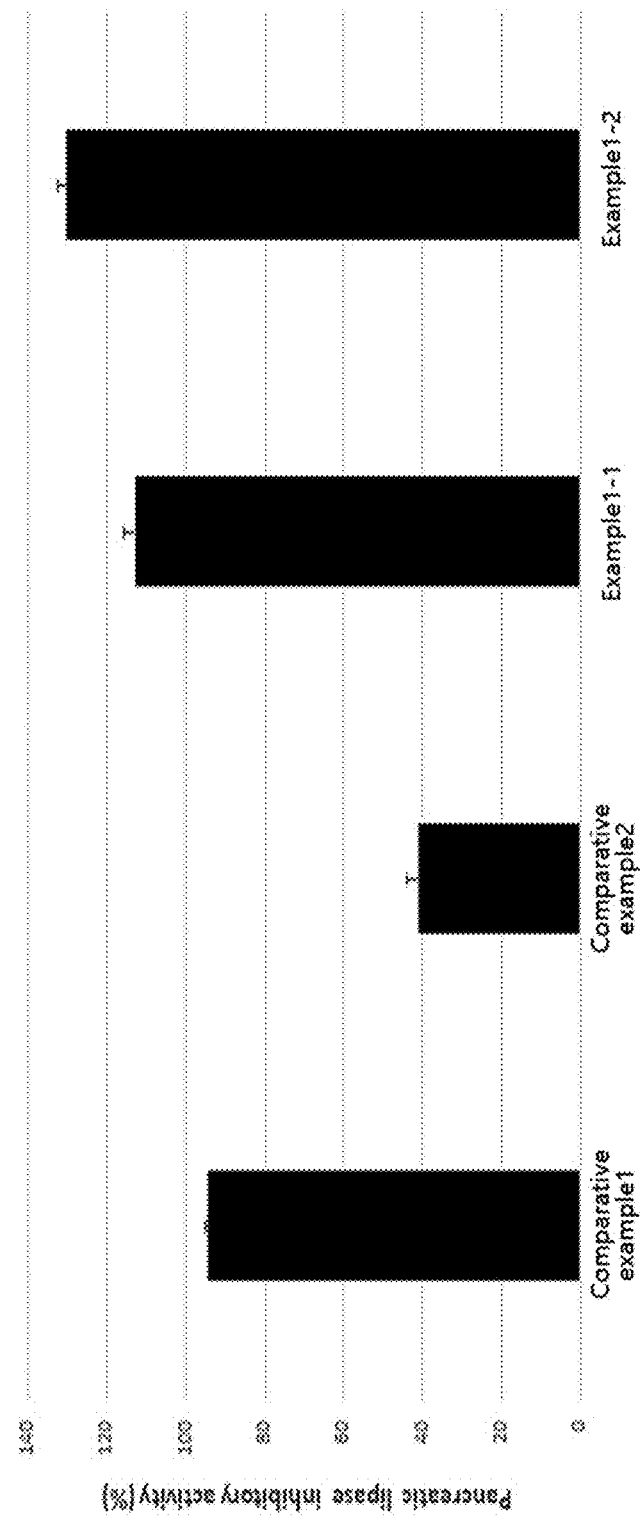
FIG. 2 is a drawing which shows the synergistic effect for the pancreatic lipase inhibitory activity of the complex of Indian gooseberry extract and barley sprout extract, compared when treated as a single substance.

Hereinafter, the present invention will be described in more detail by examples. These examples are intended to illustrate the present invention more specifically, and it will be obvious for those skilled in the art that the scope of the present invention is not limited by these examples.

Example 1. Test Substance Preparation Method 1,1 Preparation of Indian Gooseberry (Amla) Extract (Comparative Example 1)

After washing fruits of Indian gooseberry (Amla, origin Nepal) and squeezing, the Indian gooseberry fruit extract was obtained. Then, after filtering and concentrating, and then drying, the Indian gooseberry extract to be used in the present invention was prepared.

1.2 Preparation of Barley Sprout Extract (Comparative Example 2)

After harvesting barley sprout (origin Korea) and squeezing, to remove insoluble fibers such as cellulose, it was filtered and then dried. The dried powder was homogenized to prepare the barley sprout extract to be used in the present invention.

1.3 Preparation of Complexes (Examples 1 to 5)

The Indian gooseberry (Amla) extract and barley sprout extract prepared in the Comparative example 1 to Comparative example 2 were combined in a weight ratio as the following Table 1 to prepare complexes.

TABLE 1

| Classification | Combining ratio of Indian gooseberry:barley sprout | Indian gooseberry extract (% by weight) | Barley sprout extract (% by weight) |
| --- | --- | --- | --- |
| Example 1 | 1:1 | 50 | 50 |
| Example 2 | 4:1 | 80 | 20 |
| Example 3 | 2:1 | 66.67 | 33.33 |
| Example 4 | 1:2 | 33.33 | 66.67 |
| Example 5 | 1:4 | 20 | 80 |

1.4 Candidate Material Preparation Method

Through domestic and foreign document reviews, anti-obesity or anti-diabetic active materials were searched, and natural materials obtained considering the availability of domestic raw materials and availability of intake as food ingredients were selected as candidate materials and used for research. Candidate materials, A, B, C and D represent lotus leaves, balloon-flowers, *Cudrania tricuspidata* and cinnamon, respectively, and they were extracted by adding hot water and were subjected to spray drying, and then were used for research. E and F represent Mori folium and *Nelumbo nucifera*, and were extracted by adding hot water and then were concentrated and were subjected to spray drying, and were used for research. G, H and I represent beetroot, pomegranate, and tart cherry, and they were concentrated and were subjected to spray during and then were used for research.

1.5 Marker Component Content Confirmation

For the marker component content analysis and raw material standardization of the Indian gooseberry (Amla) extract and barley sprout extract, for each raw material of the Indian gooseberry (Amla) extract (Comparative example 1-1, Comparative example 1-2, Comparative example 1-3) and barley sprout extract (Comparative example 2-1, Comparative example 2-2, Comparative example 2-3), three kinds of raw materials were produced.

The marker component of the Indian gooseberry (Amla) extract was set to 'ellagic acid', and the marker component of the barley sprout extract was set to saponarin, and they were analyzed. The content of the marker component for the Indian gooseberry (Amla) extract was arranged in Table 2 and Table 3 depending on the analysis method, and the content of the marker component for the barley sprout extract was arranged in Table 4.

More specifically, analysis of the content of the marker component of each extract was conducted as follows.

The analysis method used for quantification of ellagic acid of the Indian gooseberry (Amla) extract was as follows.

The content of ellagic acid in the Indian gooseberry (Amla) extract was measured using High performance chromatography after acid hydrolysis. It was separated by a gradient method using Capcellpak C18 UG120 (4.6 mm×250 mm, 5 (mm) as a column, and using a 6:4 mixed solution of 0.85% phosphate in distilled water and methanol (A) and methanol (B) as a moving bed, and ellagic acid was detected in a wavelength of 370 nm with a UV detector. As a result, the content of ellagic acid in the Indian gooseberry (Amla) extract prepared according to the experimental method 1.1 was confirmed in the range of 1-5 mg/g.

TABLE 2

| Classification | Content of ellagic acid(mg/g) |
| --- | --- |
| Comparative example 1-1 | 3.17 |
| Comparative example 1-2 | 1.91 |
| Comparative example 1-3 | 4.65 |

In the analysis method used for quantification of free ellagic acid of the Indian gooseberry (Amla) extract, the analysis method under the condition that did not undergo acid hydrolysis was as follows.

The content of the free ellagic acid in the Indian gooseberry (Amla) extract was measured using High performance chromatography, after methanol ultrasonic extraction. It was separated by a gradient method using Capcellpak C18 UG120 (4.6 mm×250 mm, 5 μm) as a column, and using a 6:4 mixed solution of 0.85% phosphate in distilled water and methanol (A) and methanol (B) as a moving bed, and ellagic acid was detected in a wavelength of 370 nm with a UV detector. As a result, the content of free ellagic acid in the Indian gooseberry (Amla) extract prepared according to the experimental method 1.1 was confirmed in the range of 5-25 mg/g.

TABLE 3

| Classification | Content of free ellagic acid (mg/g) |
| --- | --- |
| Comparative example 1-1 | 11.73 |
| Comparative example 1-2 | 5.36 |
| Comparative example 1-3 | 24.15 |

The analysis method used for quantification of saponarin of the barley sprout extract was as follows.

The content of the saponarin in the barley sprout extract was measured using High performance chromatography. It was separated by a gradient method using Capcellpak C18 UG120 (4.6 mm×250 mm, 5 μm) as a column, and using 0.1% formic acid (A) and methanol (B) as a moving bed, and saponarin was detected in a wavelength of 340 nm with a UV detector. As a result, the content of saponarin in the barley sprout extract prepared according to the experimental method 1.2 was confirmed in the range of 6-11 mg/g.

TABLE 4

| Classification | Content of saponarin (mg/g) |
| --- | --- |
| Comparative example 2-1 | 6.56 |
| Comparative example 2-2 | 7.38 |
| Comparative example 2-3 | 10.54 |

2. Efficacy Evaluation 2.1 Pancreatic Lipase Inhibitory Activity Measurement

Pancreatic lipase is an enzyme of hydrolyzing triglyceride (TG) that is triglyceride into monoglyceride (MG) and fatty acid, and progresses fat digestion, and helps intestinal epithelial cells absorb decomposition products. Accordingly, as fat absorption into intestinal cells and digestive tracts is inhibited with decomposition of triglyceride, when the activity of pancreatic lipase is inhibited, the pancreatic lipase activity inhibitory ability is a very useful test method to predict the anti-obesity activity. In the present example, the pancreatic lipase inhibitory activity was measured as follows. At first, Tris buffer (100 mM Tris-HCl, 5 mM CaCl2. pH 7.0) 169 UL and 20 UL sample were added and mixed to 6 µL enzyme solution in which porcine pancreatic lipase was dissolved at the concentration of 0.5 g/200 mL in enzyme buffer (10 mM MOPS, 1 mM EDTA, pH6.8), and then incubated at 37° C. for 15 minutes. Then, after adding 5 µL substrate solution (10 mM of p-nitrophenylbutyrate in dimethyl formamide) and incubating at 37° C. for 30 minutes, the absorbance was measured at 405 nm using a UV-visible spectrophotometer. The pancreatic lipase inhibitory activity (%) was shown in the following equation 1, and X indicates the absorbance with a sample added, and Y indicates the absorbance without a sample added. The measured value was shown as a mean value of three repeated experiments.

$$\text{Pancreatic lipase inhibitory activity (\%)} = (1-(X-Y)/Y) \times 100 \quad \text{Equation 1}$$

2.2 Confirmation of Synergistic Effect of Complex for Pancreatic Lipase Inhibitory Activity To investigate the synergistic effect of the pancreatic lipase inhibitory ability of the complex of the Indian gooseberry extract and barley sprout extract of the present invention compared to the case of treating as a single substance, the activity of the single substance and complex was analyzed at the same concentration, and to confirm the synergistic effect of the complex, Colby equation was utilized. Colby equation was shown in the following Equation 2, and the synergistic effect could be recognized when the measured value exceeded the E value derived by Colby equation. E indicates the predicted effect of the complex (A+B), and A indicates the effect of the single substance A (%), and B indicates the effect of the single substance B (%).

$$E = A+B-(AB/100) \quad \text{Equation 2}$$

2.3 Cell Culture and Differentiation Induction

The effect that the complex of the Indian gooseberry extract and barley sprout extract of the present invention affected fat synthesis and fat decomposition in the adipocyte differentiation process compared to the case of treating as a single substance was confirmed. In the present example, 3T3-L1 cell was distributed from American Type Cultured Collection (ATCC; Rockville, MD, USA) and experimented. The 3T3-L1 preadipocyte was cultured in an incubator at 37° C. and 5% CO2 (Thermo Fisher Scientific Inc., Pittsburgh, PA, USA) using high-glucose Dulbeco's modified Eagle's medium (DMEM) containing 10% newborn calf serum (NCS) and 1% penicillin-streptomycin, 1% L-glutamine, 1% sodium pyruvate, 1% hepes, and 1% NEAA mixture, and the culture solution was replaced per 2 days, and when the cell was attached 80% or more on the bottom of the flask as a single layer, the cell surface was washed using PBS solution, and after adding 0.25% trypsin-EDTA, it was left in the incubator for 3 minutes and the cells were separated. Then, the cells were collected by centrifugation at 1600 rpm for 5 minutes using a centrifuge (GYROZEN 416G), and for differentiation of cells, cells of $1 \times 10^5$ cells/well were equally aliquoted in a 6-well plate (TPP) using DMEM culture solution comprising, and 10% fetal bovine serum (FBS) and 1% penicillin-streptomycin, 1% L-glutamine, 1% sodium pyruvate, 1% hepes, 1% NEAA mixture, gentamycin, and when 100% confluent, induction of differentiation was initiated by mixing 3-isobutyl-1-methylxanthine (IBMX, 0.5 mM), insulin (10 µg/mL), and dexamethasone (DEX, 1 µM), which were the adipogenic cocktail (MDI solution), in DMEM culture solution containing 10% FBS and 1% penicillin-streptomycin, 1% L-glutamine, 1% sodium pyruvate, 1% hepes, 1% NEAA mixture and gentamycin. The differentiation period lasted 9 days in total, and for the first 3 days of differentiation, the same culture solution was replaced, and for the middle 3 days of differentiation, the culture solution was replaced with DMEM comprising 10% FBS containing only Insulin (10 µg/mL) every day, and for the latter 3 days of differentiation, it was replaced with DMEM culture solution containing 10% FBS every day. In the lipogenesis mechanism, the sample was treated at the same time as the start of differentiation every day, and in the lipolysis mechanism, it was treated for 3 days from 3 days before the end of differentiation.

2.4 Confirmation of synergistic effect of complex for intercellular cAMP level

CAMP is involved in promoting triglyceride decomposition and promoting heat generation by activating hormone sensitive lipase (HSL) which is lipase. In the present example, to measure the intercellular cAMP level, cAMP ELISA kit (Cell biolabs Inc., San Diego, CA USA) was used, and it was measured as follows. At first, $1 \times 10^6$ cell was added to lysis buffer and homogenized, and centrifuged at 13,000 rpm for 5 minutes, and the supernatant was used as a sample. The sample and standard reagent were aliquoted by 50 µL in each well, and Peroxidase CAMP Tracer Conjugate reagent was aliquoted by 25 µL and then Rabbit Anti-CAMP Polyclonal Antibody reagent was aliquoted by 50 µL, and was left at room temperature for 2 hours placing a plate cover. In 2 hours, it was aliquoted by 250 µL with wash buffer, and a total of 5 washing operations were conducted, and 100 µL of the substrate solution warmed at a room temperature was aliquoted in each well, and then it was left at a room temperature for 20 minutes. In 20 minutes, stop solution 100 µL was aliquoted in each well to stop the reaction, and the absorbance was measured at the 450 nm wavelength.

2.5 Confirmation of Synergistic Effect of Complex for Intercellular Glycerol Release Fat decomposition is a process that triglyceride in adipocytes is hydrolyzed into free acid and glycerol, and to confirm the effect on fat decomposition in adipocytes, glycerol to be increased during fat decomposition was measured. In the present example, to measure the effect on the amount of glycerol released in the process of differentiation of adipocytes, the glycerol content in the culture solution was measured using a free glycerol reagent applying glycerol phosphate oxidase-TRINDER enzyme reaction method by the method such as McGowan, and the like, and it was measured as follows. At first, each sample was treated by concentration, and each culture solution was collected and used at the latter of differentiation (Day 9), respectively, and the culture solution (1 mL) and free glycerol reagent (800 μL) were mixed and were reacted in a 37° C. hot plate for 10 minutes, and then the optical density was measured at the 540 nm wavelength using ELISA reader (Molecular Devices, USA). The glycerol content was measured by preparing a standard curve using free glycerol as a standard reagent, and the protein content was measured using BSA as a standard reagent by Bradford method.

2.6 Confirmation of Synergistic Effect of Complex for Intercellular IRS, PI3K and GLUT4

IRS (Insulin receptor substrate) is an insulin receptor substrate distributed in systemic tissue, and is involved in the insulin signaling pathway and regulates glucose and lipid metabolism, and PI3K (Phosphoinositide 3-Kinase) is an enzyme which is involved in the insulin signaling pathway, and functions to regulate blood sugar absorption and inhibit fat synthesis by interacting with IRS. GLUT4 (Glucose transport 4) is a glucose receptor mostly present in adipocytes and muscle cells, and promotes glucose transport from cells to cell membranes by the action of insulin. When insulin resistance occurs by visceral fat accumulation, GLUT4 translocation from cytoplasm into cell membranes does not occur smoothly. In the present example, to measure the protein expression of IRS, PI3K and GLUT4, protein quantification of cell lysate of western blotting was conducted using Bradford assay. Protein (40 μg) was loaded in 10% Mini-PROTEAN® TGX™ Precast Gels (Bio-Rad), and transferring was progressed using Trans-Blot® Turbo™ Transfer system (Bio-Rad). The membrane was blocked in blocking buffer (5% skim milk in Tris buffered saline with 1% Tween® 20) for 1 hour, and after washing, it was reacted with IRS, PI3K and GLUT4 primary antibodies. After washing and reacting the HRP-polymerized secondary antibody (Cell Signaling, 1:3000) for 1 hour, and then it was washed and color was developed using EzWest Lumi plus (ATTO, Tokyo, Japan), and it was analyzed using Ez-Capture II (ATTO) and CS Analyzer 3.0 software (ATTO).

2.7 Confirmation of Synergistic Effect of Complex for Inhibition of Intercellular Fat Accumulation To measure the effect on adipocyte differentiation in the process of differentiating from preadipocytes to adipocytes of the complex of the Indian gooseberry extract and barley sprout extract of the present invention, Oil red O staining was performed. In other words, according to the cell culture and differentiation induction protocol, the DMEM culture solution containing 10% FBS comprising the adipogenic cocktail and the extract were replaced every day, and at the latter of differentiation (Day 9), Oil red O staining was conducted, respectively. The culture solution was sucked, and it was washed with PBS solution twice and then PBS solution was completely sucked, and 10% formalin was added and fixed at a room temperature for 5 minutes, and then 10% formalin was sucked, and new 10% formalin was added again, and fixed at a room temperature for 2 hours or more. Then, formalin was sucked, and 60% isopropanol was added and sucked immediately, and then the flask was completely dried, and Oil red O solution was added to stain fat globules for 60 minutes. After staining, they were washed with distilled water 4 times and intercellular accumulation of the fat globules was observed with a microscope and a camera. To qualify the contents of fat globule accumulation, 100% isopropanol was added under the well dried condition, and Oil red O dye was eluted, and then the optical density was measured at the 520 nm wavelength using ELISA reader (Molecular Devices, USA). Then, 100% isopropanol was used as blank.

2.8 Confirmation of Effect on Body Weight Change of Obesity-Induced Mice of Complex The effect on the body weight change of obesity-induced mice from high fat diet of the complex of the Indian gooseberry extract and barley sprout extract of the present invention was confirmed. As an experimental animal, 4-week male C57BL/6J mice around 20 g were supplied from Saeron Bio Inc. (Uiwang-si, Korea). They were used for the experiment, after passing through the adaptation period for 1 week under the condition that the light and dark was 12 hours (light/dark cycle) and the temperature was 23±2° C. and the relative humidity was 50±5%. During the adaptation period, AIN-93G diet and drinking water were allowed to be consumed freely, and the body weight was measured to separate 8 mice per each group by the random method. At the end of the adaptation period, the sample intake was progressed as free diet intake for 15 weeks, and the dietary intake and body weight were measured every week, and after the end of the experiment, the weight gain was divided by the dietary intake (total food consumption)) for the same period to calculate the food efficiency ratio (FER). The classification of the experimental group and the composition of the experimental diet were shown in Table 5, and the equation of the diet efficiency was shown in the following equation 3.

$$\text{FER} = \text{weight gain (g)/total food consumption (g)} \times 100 \qquad \text{Equation 3}$$

TABLE 5

| Experimental group | Experimental diet |
| --- | --- |
| Normal group (NC) | AIN 93G diet |
| Control group (C) | 60% high fat diet |
| Positive control group (Met) | 60% high fat diet + Metformin 250 mg/kg b.w. |
| Example 3 100 mg/kg | 60% high fat diet + IG:BP (2:1) 100 mg/kg b.w. |
| Example 3 200 mg/kg | 60% high fat diet + IG:BP (2:1) 200 mg/kg b.w. |
| Example 3 400 mg/kg | 60% high fat diet + IG:BP (2:1) 400 mg/kg b.w. |

2.9 Confirmation of Effect on Organ and Fat Tissue Weight Change of Obesity-Induced Mice of Complex The effect on the organ and fat tissue weight change of obesity-induced mice from high fat diet of the complex of the Indian gooseberry extract and barley sprout extract of the present invention was confirmed. For tissue excision, after blood-gathering, organ (liver, kidney, spleen) and white fat tissue (subcutaneous fat, visceral fat (epididymal fat and intraperitoneal fat)) were excised, and then were washed with physiological saline solution and moisture was removed with filter paper, and then the weight was measured.

2.10 Confirmation of Effect on Change of Glucose, Insulin and HbA1c in Blood of Obesity-Induced Mice of Complex The effect on the change of Glucose, Insulin and HbA1c in blood of obesity-induced mice from high fat diet of the complex of the Indian gooseberry extract and barley sprout extract of the present invention was confirmed. For blood analysis, at the end of the experiment, the experimental animals were anesthetized with isoflurane after 12 hours of fasting, and blood was collected through the hepatic vein, and the blood was analyzed by whole blood and serum separated by centrifugation (14,000 rpm, 20 min, 4° C.), and was measured using ELISA kit (Biovision).

3. Experimental Result 3-1. Pancreatic Lipase Inhibitory Activity for 11 Kinds of Natural Substances The pancreatic lipase inhibitory activity for 11 kinds of natural substances prepared by the preparation method suggested in the experimental method was measured. As suggested in FIG. 1 and Table 6, it was confirmed that the lipase inhibitory activity of the sample of Comparative example 1 was the highest as 83.77±0.27% at the same concentration, and it was confirmed that the lipase inhibitory activity of the sample of Comparative example 2 was excellent as 42.81±2.09% next. This result confirmed that in the pancreatic lipase inhibitory activity for 11 kinds of natural substances, the Indian gooseberry extract and barley sprout extract were the most excellent, and the Indian gooseberry extract and barley sprout extract reduced the fat absorption in the body by acting as a pancreatic lipase inhibitor, and retained the anti-obesity activity.

TABLE 6

| Classification | Sample | Pancreatic lipase inhibitory ability (%) |
|---|---|---|
| A | lotus leaves | 25.36 |
| B | balloon-flowers | 13.48 |
| C | Cudrania tricuspidata | 36.75 |
| Comparative example 1 | Indian gooseberry | 83.77 |
| D | Cinnamon | 14.39 |
| E | Mori folium | 14.75 |
| F | Nelumbo nucifera | 1.05 |
| G | Beetroot | 13.62 |
| H | Pomegranate | 31.97 |
| I | Tart cherry | 26.91 |
| Comparative example 2 | Barley sprout | 42.81 |

3-2. Synergistic Effect of Complex of Indian Gooseberry and Barley Sprout for Pancreatic Lipase Inhibitory Activity The pancreatic lipase inhibitory activity for the single substance and complex of the Indian gooseberry extract and barley sprout extract prepared by the preparation method suggested in the experimental method was measured. The pancreatic lipase inhibitory activity of the Indian gooseberry extract was indicated by Comparative example 1, and the pancreatic lipase inhibitory activity of the barley sprout extract was indicated by Comparative example 2, and the pancreatic lipase inhibitory activity of the complex at the same concentration was represented by Example 1-1, and the result measured by utilizing Colby equation to confirm the synergistic effect of the complex was represented by Example 1-2. As suggested in Table 2 and Table 7, the pancreatic lipase inhibitory activity of the Indian gooseberry extract was 94.42±0.66%, and the barley sprout extract showed efficacy of 40.83±3.14%, and the pancreatic lipase inhibitory activity of the complex at the same concentration was 112.64±3.20%, and the pancreatic lipase inhibitory activity of the complex was more excellent than the single substance. The expected value of the synergistic effect of the complex derived using Colby equation was 96.70%, and Example 1-2 shows an excellent effect of 130.06±2.21% about 134% or more then the expected value. This confirmed that the complex of the Indian gooseberry extract and barley sprout extract had a significantly synergistic effect in inhibiting the enzymatic activity of pancreatic lipase than each single substance, and inhibited digestion and absorption of ingested fat and retained the anti-obesity activity.

TABLE 7

| Classification | Sample | Concentration (mg/mL) | Pancreatic lipase inhibitory ability (%) |
|---|---|---|---|
| Comparative example 1 | Indian gooseberry extract | 50 | 94.42 |
| Comparative example 2 | Barley sprout extract | 50 | 40.83 |
| Example 1-1 | 1:1 Mixture of Indian gooseberry extract and barley sprout extract | 50 | 112.64 |
| Example 1-2 | 1:1 Mixture of Indian gooseberry extract and barley sprout extract | 100 | 130.06 |

Figure 3:
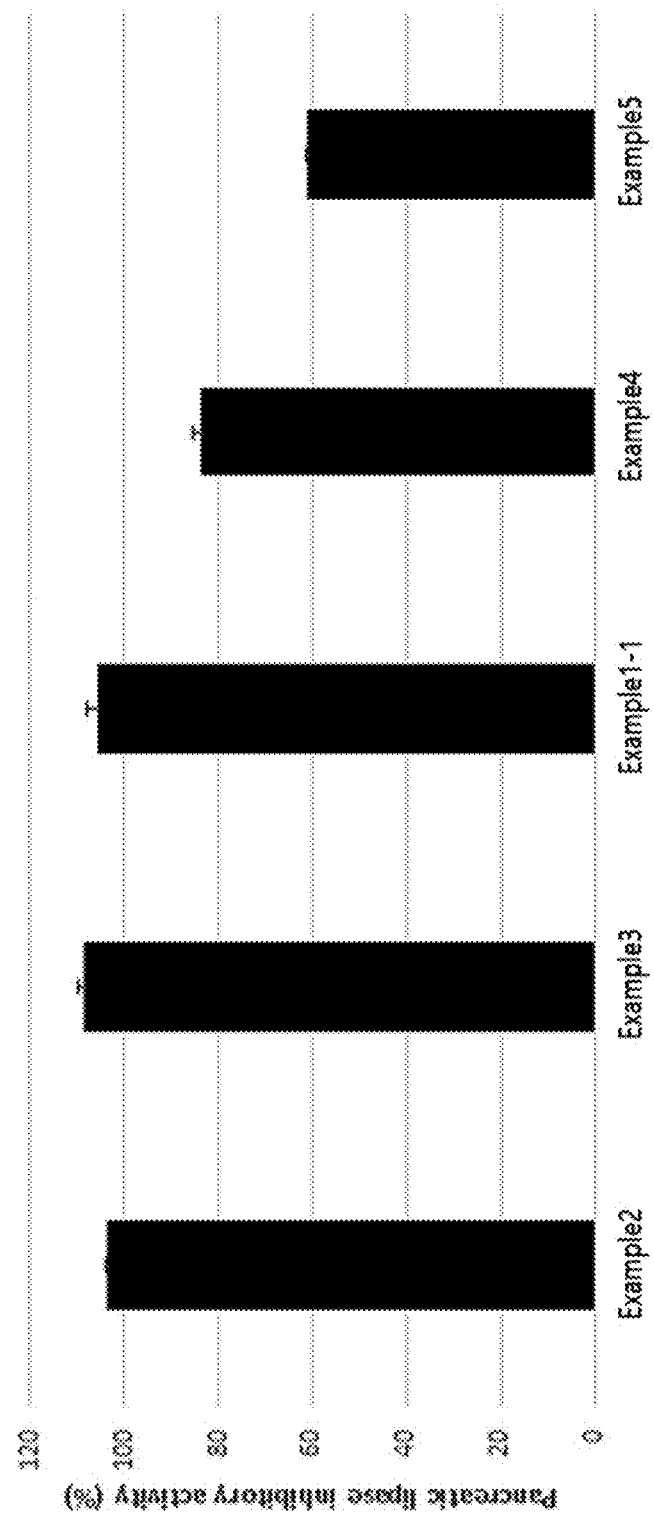
FIG. 3 is a drawing which shows the pancreatic lipase inhibitory activity depending on the mixing ratio of the Indian gooseberry extract and barley sprout extract.

3-3. Confirmation of Indian Gooseberry and Barley Sprout Complex Combined in Various Weight Ratios on Pancreatic Lipase Inhibitory Activity To select the optimal ratio of the complex of the Indian gooseberry extract and barley sprout extract prepared by the preparation method suggested in the experimental method, the pancreatic lipase inhibitory activity was measured. According to the experimental result 3-2, by confirming that the Indian gooseberry and barley sprout showed the synergistic effect in the complex than each single substance, the preparation process and economic feasibility were considered, and then the optimal ratio which the complex of the Indian gooseberry and barley sprout showed the most excellent efficacy was to be selected. As suggested in FIG. 3 and Table 8, the pancreatic lipase inhibitory activity according to the mixing ratio of the Indian gooseberry and barley sprout at the same concentration was 103.45±2.14, 108.37±1.92 and 105.62±0.40, respectively, at 4:1, 2:1 and 1:1 of the ratio of Indian gooseberry and barley sprout, which was similar, and was more excellent than 83.30±1.63 and 60.98±0.33 measured at 1:2 and 1:4. By the result, it was confirmed that the complex of the Indian gooseberry extract and barley sprout extract having a significantly synergistic effect than each single substance could inhibit digestion and absorption of fat by acting as an excellent pancreatic lipase inhibitor in the ratio of Indian gooseberry:barley sprout of 4:1~1:1 than any other mixing ratio.

TABLE 8

| Classification | Indian gooseberry:barley sprout mixing ratio | Concentration (mg/mL) | Pancreatic lipase inhibitory activity (%) |
|---|---|---|---|
| Example 2 | 4:1 | 50 | 103.45 |
| Example 3 | 2:1 | 50 | 108.37 |
| Example 1 | 1:1 | 50 | 105.62 |
| Example 4 | 1:2 | 50 | 83.30 |
| Example 5 | 1:4 | 50 | 60.98 |

Figure 4:
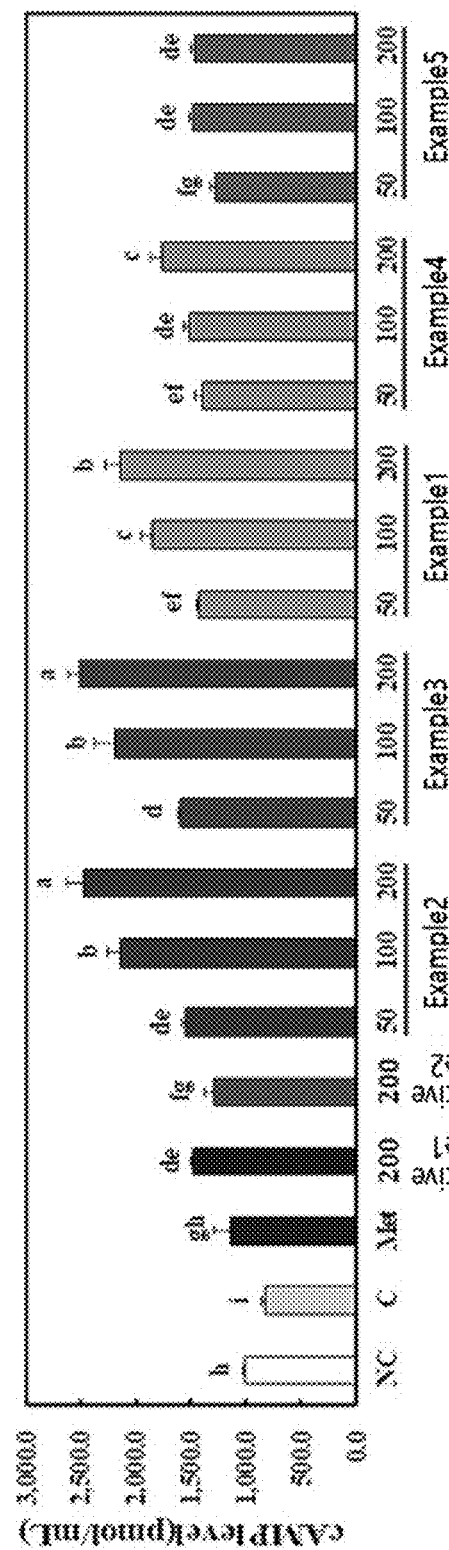
FIG. 4 is a drawing which shows the intracellular CAMP level depending on the mixing ratio of the Indian gooseberry extract and barley sprout extract.

3-4. Confirmation of Effect of Indian Gooseberry and Barley Sprout Combined in Various Weight Ratios for Intercellular cAMP Level The intercellular CAMP level was measured by combining the Indian gooseberry extract and barley sprout extract prepared by the preparation method suggested in the experimental method in various weight ratios. As suggested in FIG. 4, the single substance of the Indian gooseberry and barley sprout showed the activity of 1479.3±16.8 and 1300.0±81.9, respectively, at the same concentration, and the CAMP level according to the mixing ratio of Indian gooseberry and barley sprout was 2472.3±163.8 and 2508.3±106.3, at the ratio of Indian gooseberry:barley sprout of 4:1 and 2:1, respectively, and a significantly synergistic effect was shown compared to the single substance. Subsequently, the excellent activity was shown in order of 2132.7±149.4, 1763.7±101.1 and 1469.7±24.5 measured at 1:1, 1:2 and 1:4. By the result, it was confirmed that the complex of the Indian gooseberry extract and barley sprout extract having a significantly synergistic effect than each single substance could promote fat decomposition through CAMP expression regulation.

Figure 5:
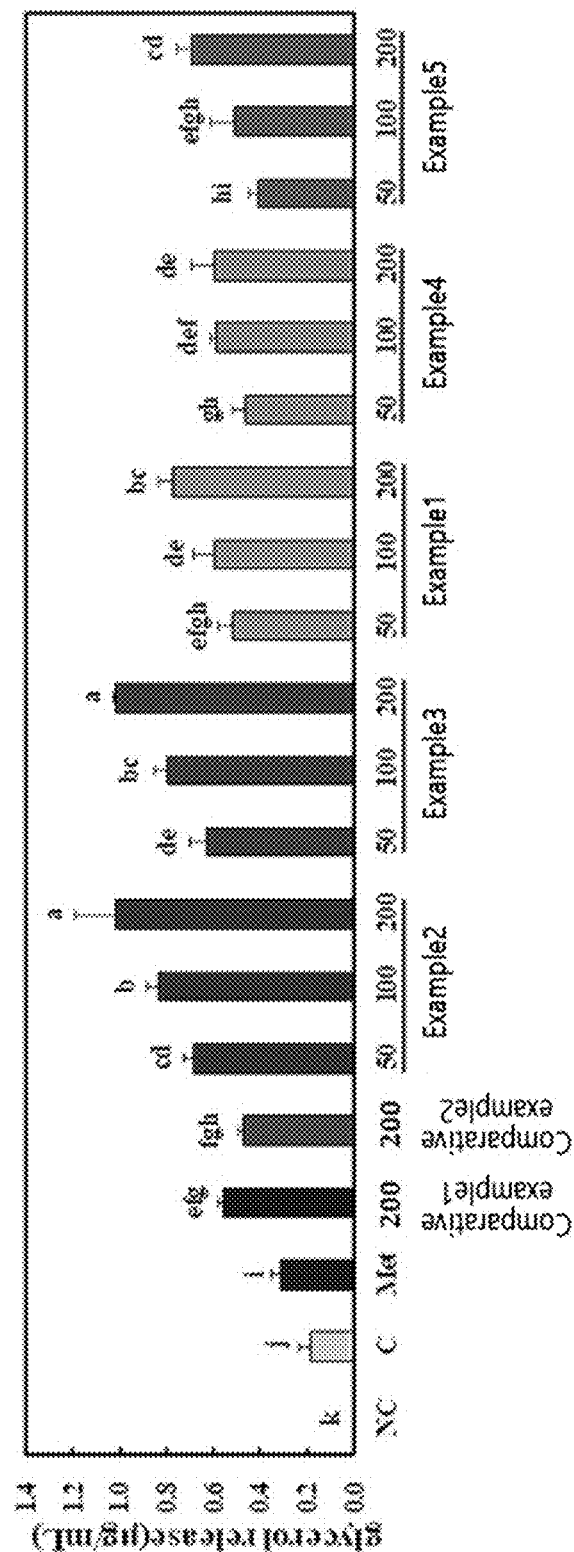
FIG. 5 is a drawing which shows the intracellular glycerol release depending on the mixing ratio of the Indian gooseberry extract and barley sprout extract.

3-5. Confirmation of Effect of Indian Gooseberry and Barley Sprout Complex Combined in Various Weight Ratios for Intercellular Glycerol Release The intercellular glycerol release was measured by combining the Indian gooseberry extract and barley sprout extract prepared by the preparation method suggested in the experimental method in various weight ratios. As suggested in FIG. 5, the single substance of Indian gooseberry and barley sprout showed the activity of 0.55±0.03 and 0.47±0.03, respectively, at the same concentration, and the glycerol release according to the mixing ratio of Indian gooseberry and barley sprout was 1.01±0.17 and 1.01±0.01, respectively, at the ratio of Indian gooseberry:barley sprout of 4:1 and 2:1, which was a significantly synergistic effect, compared to the single substance. Subsequently, the excellent activity was shown in order of 0.77±0.06, 0.69±0.06 and 0.60±0.09 measured at 1:1, 1:4 and 1:2. By the result, it was confirmed that the complex of the Indian gooseberry extract and barley sprout extract having a significantly synergistic effect than each single substance decomposed triglyceride, that is neutral fat, present in fat globules accumulated in adipocytes, thereby increasing the glycerol release.

3-6. Synergistic Effect of Indian Gooseberry and Barley Sprout Complex for Intercellular IRS1

Figure 6:
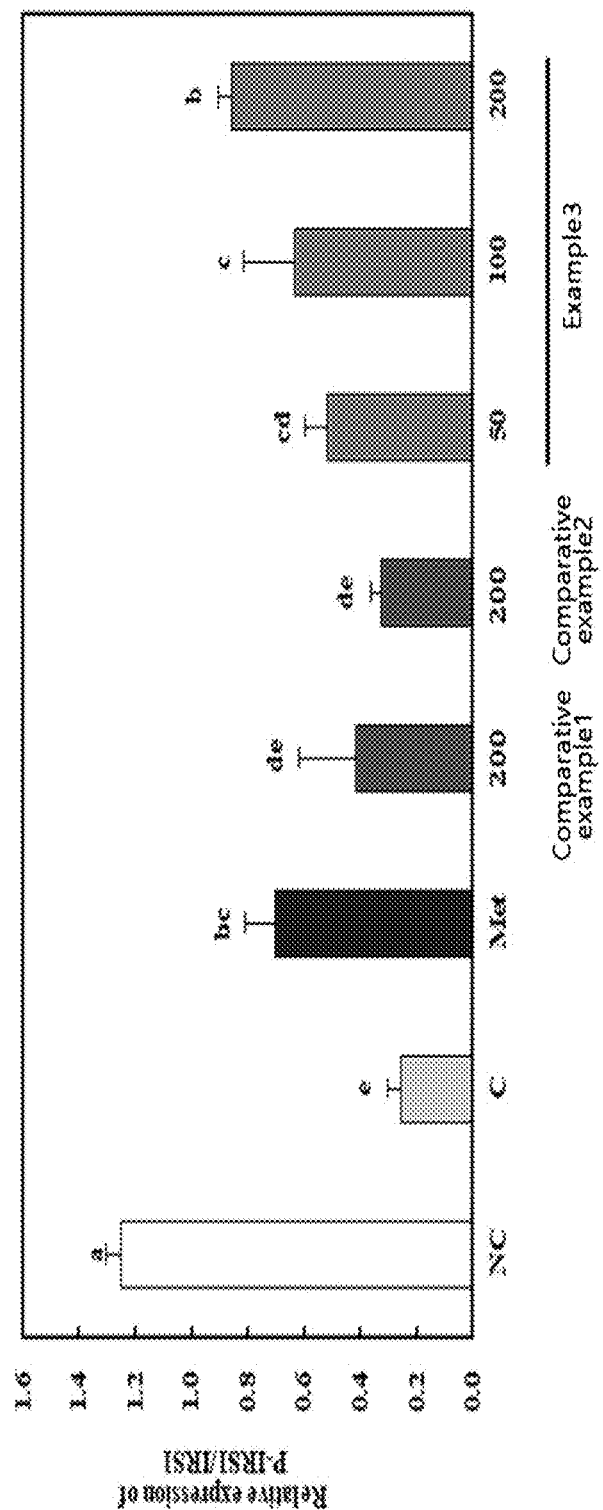
FIG. 6 is a drawing which shows the synergistic effect for the protein expression ratio of intracellular P-IRS1/IRD1 of the complex of Indian gooseberry extract and barley sprout extract, compared when treated as a single substance.

The expression ratio of the intercellular P-IRS1/IRS1 was confirmed by combining the Indian gooseberry extract and barley sprout extract prepared by the preparation method suggested in the experimental result. As suggested in FIG. 6, the single substance of Indian gooseberry and barley sprout showed the expression ratio of 0.42 and 0.32, respectively, at the same concentration, and the complex of Indian gooseberry and barley sprout, Example 3 showed a significantly synergistic effect compared to the single substance, as the expression ratio of 0.86. In addition, the treatment group of 50, 100 μg/mL showed the expression ratio of 0.51 and 0.63, respectively, and the complex of Indian gooseberry and barley sprout increased the expression ratio of the intercellular P-IRS1/IRS1 in the concentration dependent way, and by the result, it was confirmed that the complex of the Indian gooseberry extract and barley sprout extract could regulate blood sugar absorption and inhibit fat synthesis from glucose metabolism by increasing the expression ratio of P-IRS1/IRS1.

Figure 7:
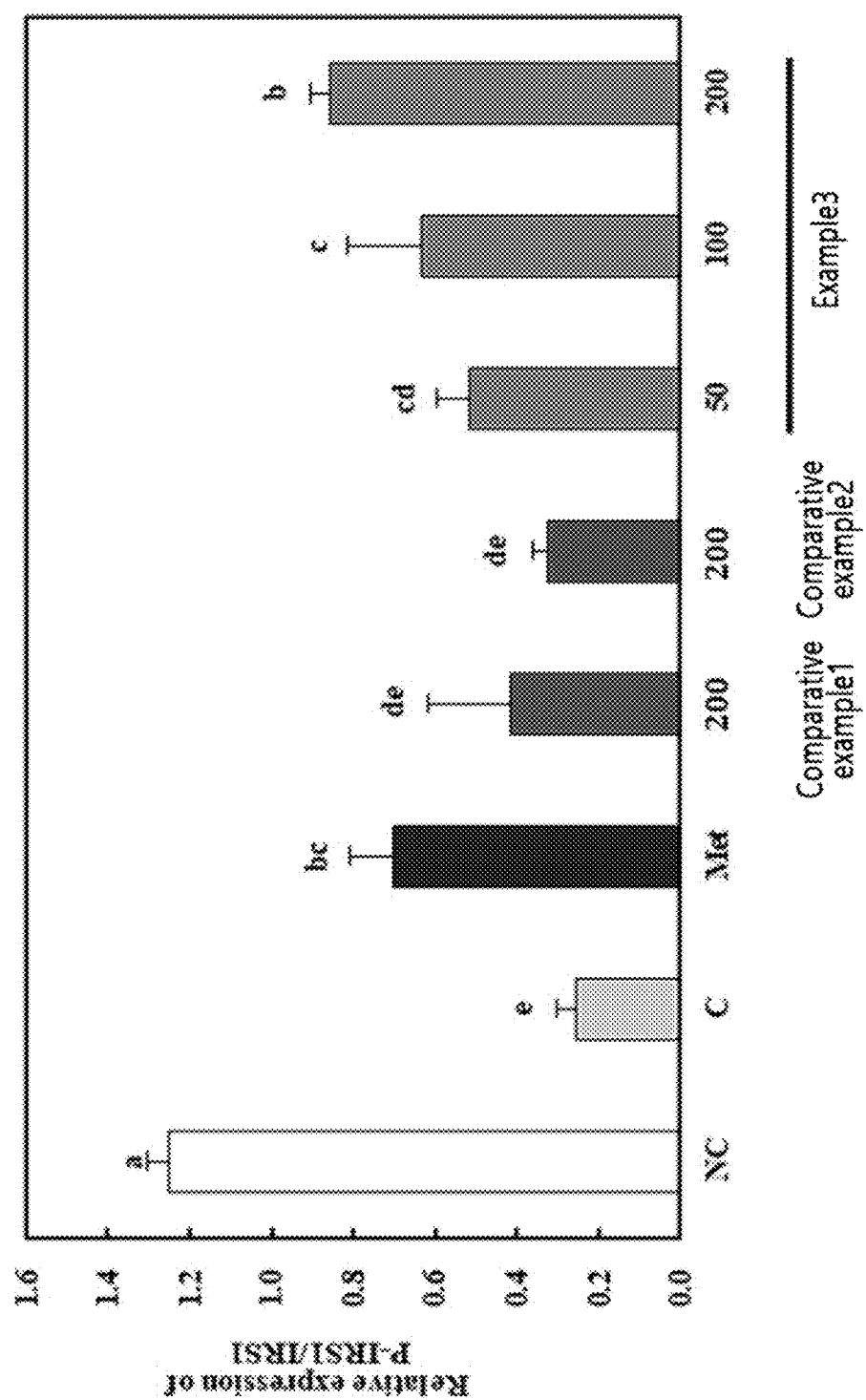
FIG. 7 is a drawing which shows the synergistic effect for the protein expression ratio of intracellular P-PI3K/PI3K of the complex of Indian gooseberry extract and barley sprout extract, compared when treated as a single substance.

3-7. Synergistic Effect of Indian Gooseberry and Barley Sprout Complex for Intercellular PI3K The expression ratio of the intercellular P-PI3K/PI3K was confirmed by combining the Indian gooseberry extract and barley sprout extract prepared by the preparation method suggested in the experimental result. As suggested in FIG. 7, the single substance of Indian gooseberry and barley sprout showed the expression ratio of 1.93 and 1.26, respectively, at the same concentration, and the complex of Indian gooseberry and barley sprout, Example 3 showed a significantly synergistic effect compared to the single substance, as the expression ratio of 4.31. In addition, the treatment group of 50, 100 μg/mL showed the expression ratio of 1.05 and 1.47, respectively, and the complex of Indian gooseberry and barley sprout increased the expression ratio of the intercellular P-PI3K/PI3K in the concentration dependent way, and by the result, it was confirmed that the complex of the Indian gooseberry extract and barley sprout extract could regulate blood sugar absorption and inhibit fat synthesis from glucose metabolism.

3-8. Synergistic Effect of Indian Gooseberry and Barley Sprout Complex for Intercellular GLUT4

Figure 8:
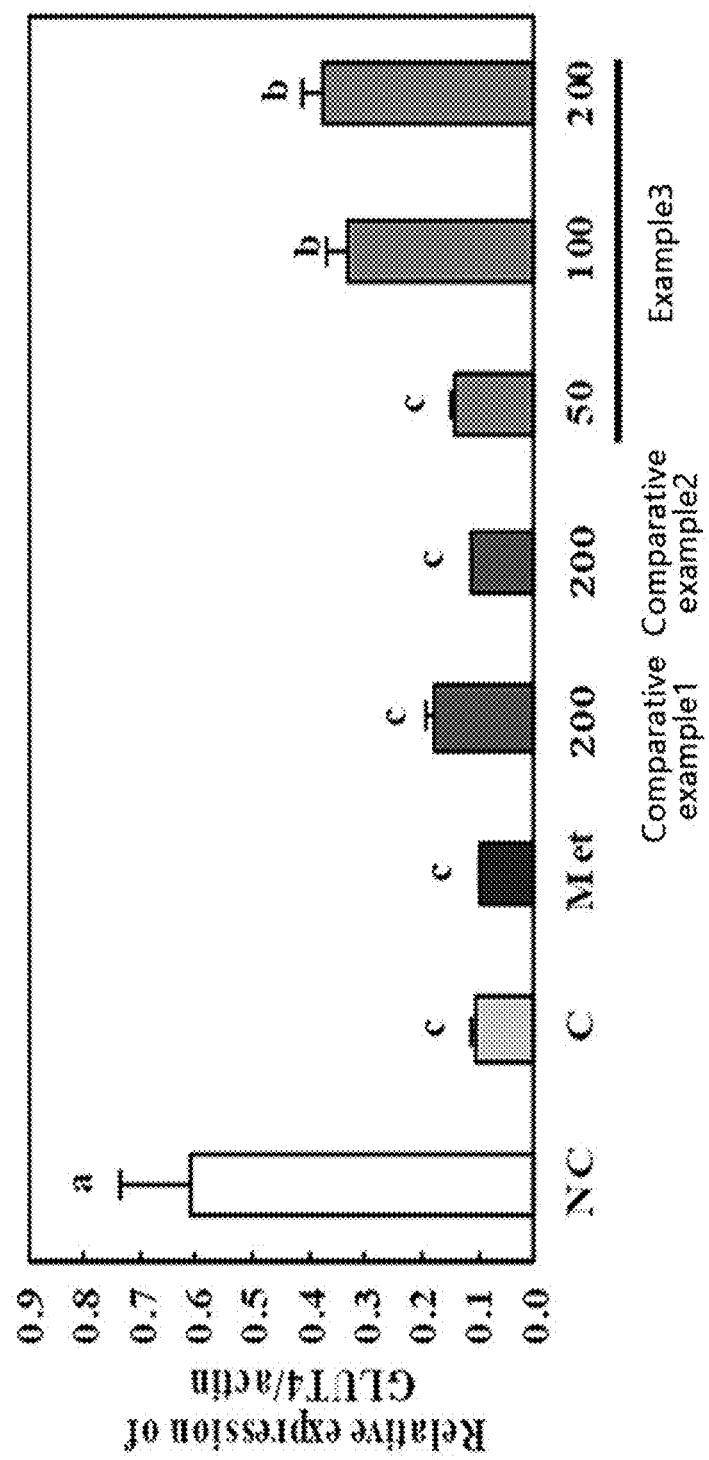
FIG. 8 is a drawing which shows the synergistic effect for the protein expression ratio of intracellular GLUT4 of the complex of Indian gooseberry extract and barley sprout extract, compared when treated as a single substance.

The expression ratio of the intercellular GLUT4 was confirmed by combining the Indian gooseberry extract and barley sprout extract prepared by the preparation method suggested in the experimental result. As suggested in FIG. 8, the single substance of Indian gooseberry and barley sprout showed the expression ratio of 0.18 and 0.11, respectively, at the same concentration, and the complex of Indian gooseberry and barley sprout, Example 3 showed a significantly synergistic effect compared to the single substance, as the expression ratio of 0.38. In addition, the treatment group of 50, 100 ug/mL showed the expression ratio of 0.14 and 0.33, respectively, and the complex of Indian gooseberry and barley sprout increased the expression ratio of the intercellular GLUT4 in the concentration dependent way, and by the result, it was confirmed that the complex of the Indian gooseberry extract and barley sprout extract could regulate blood sugar absorption and inhibit fat synthesis from glucose metabolism by promoting GLUT4 signaling.

Figure 9:
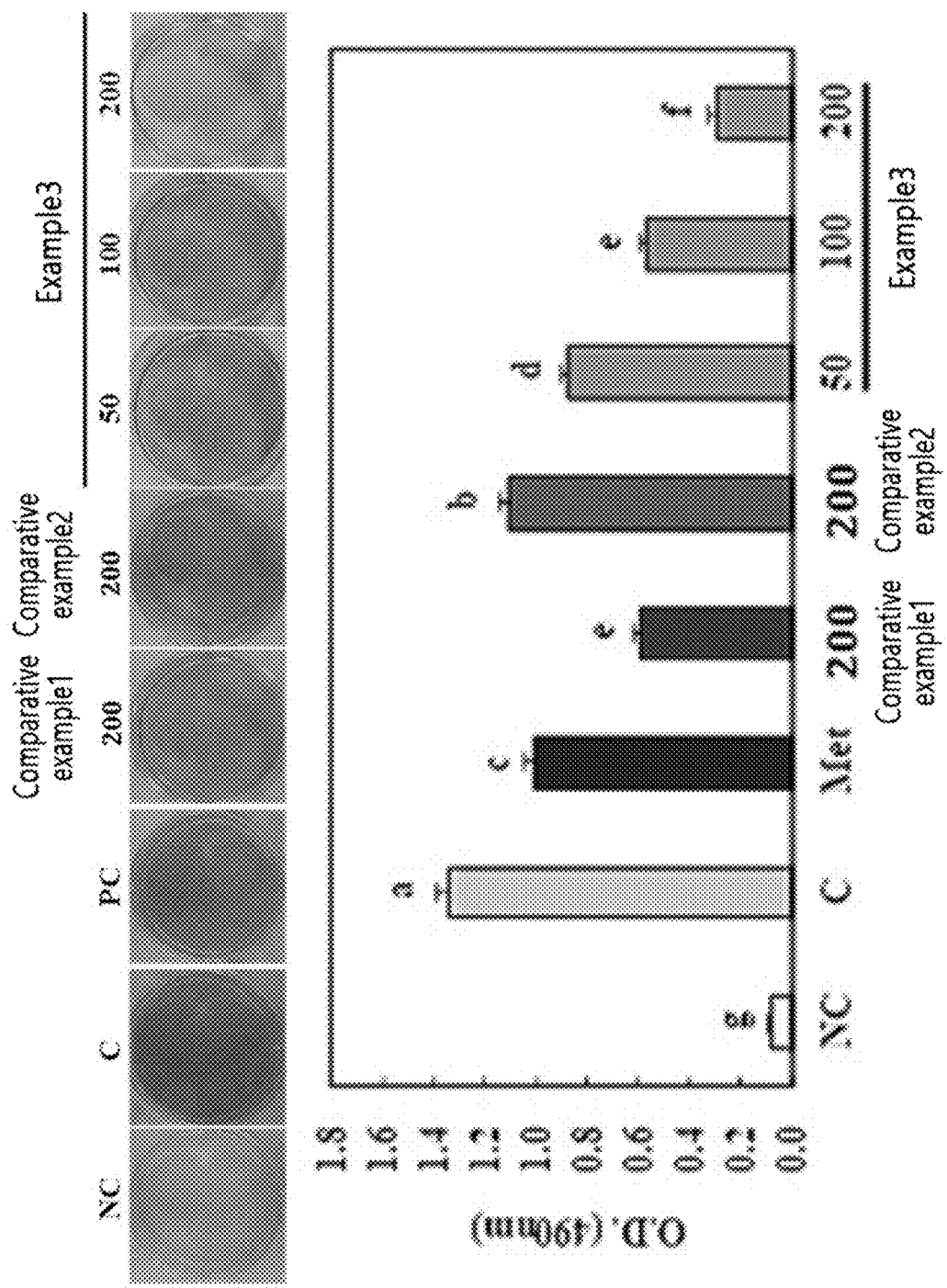
FIG. 9 is a drawing which shows the synergistic effect for inhibition of intracellular fat accumulation of the complex of Indian gooseberry extract and barley sprout extract, compared when treated as a single substance.

3-9. Synergistic Effect of Indian Gooseberry and Barley Sprout Complex for Inhibition of Intercellular Fat Accumulation Oil red O staining was performed to measure the effect on adipocyte differentiation by combining the Indian gooseberry extract and barley sprout extract prepared by the preparation method suggested in the experimental method. As suggested in FIG. 9, the single substance of Indian gooseberry and barley sprout showed the content of intercellular triglyceride of 0.60±0.02 and 1.10±0.05, respectively, at the same concentration, and the complex of Indian gooseberry and barley sprout, Example 3 was 0.29±0.03, and a significantly synergistic effect compared to the single substance was shown. In addition, in the treatment group of 50, 100 μg/mL, it was 0.88±0.02 and 0.57±0.03, respectively, and it was confirmed that the complex of Indian gooseberry and barley sprout inhibited fat accumulation in adipocytes in the concentration dependent way.

3-10. Confirmation of Effect on Weight Change of Obesity-Induced Mice of Indian Gooseberry and Barley Sprout Complex To confirm the effect on the weight change of obesity-induced mice from high fat diet by combining the Indian gooseberry extract and barley sprout extract prepared by the preparation method suggested in the experimental method, the body weight of the experimental animals was measured. As suggested in Table 9, The control group in which obesity was induced by high fat diet showed the weight increase of 30.92±3.53, and the complex of Indian gooseberry and barley sprout, Example 3 showed the concentration-dependent body weight reduction, as 28.13±3.93, 25.78±3.35 and 24.70±1.85, respectively, according to the administration groups of 100, 200 and 400 mg/kg. Also in the result of comparing the diet efficiency, it was confirmed that it was reduced in the Indian gooseberry and barley sprout complex in the concentration dependent way, compared to the control group, and thereby it was confirmed that the complex of the Indian gooseberry extract and barley sprout extract showed an excellent effect in body weight reduction.

TABLE 9

| Groups | NC | C | Met | HFD supplementation | | |
|---|---|---|---|---|---|---|
| | | | | Example3 100 | Example3 200 | Example3 400 |
| Initial body weight (g) | 19.11 ± 0.23$^{ra}$ | 19.35 ± 0.84 | 19.26 ± 0.66 | 19.40 ± 0.72 | 19.57 ± 0.40 | 18.82 ± 0.53 |
| Final body weight (g) | 32.24 ± 3.74$^a$ | 50.27 ± 3.67$^a$ | 39.46 ± 2.16$^d$ | 47.53 ± 3.56$^{ab}$ | 45.35 ± 3.30$^{bc}$ | 43.52 ± 2.16$^c$ |
| Weight gain (g)* | 13.13 ± 3.67$^d$ | 30.92 ± 3.53$^a$ | 20.20 ± 1.89$^c$ | 28.13 ± 3.93$^{ab}$ | 25.78 ± 3.35$^b$ | 24.70 ± 1.85$^b$ |
| Food intake (g/day/mouse) | 2.49 ± 0.19$^c$ | 2.91 ± 0.23$^a$ | 2.66 ± 0.18$^b$ | 2.89 ± 0.18$^a$ | 2.98 ± 0.21$^a$ | 2.71 ± 0.20$^b$ |
| FER** | | 5.03 ± 1.41$^d$ | 10.12 ± 1.15$^a$ | 7.25 ± 0.68$^c$ | 9.28 ± 1.30$^{ab}$ | 8.25 ± 1.07$^{bc}$ | 8.68 ± 0.65$^b$ |

3-11. Confirmation of Effect on Organ and Fat Tissue Weight Change of Obesity-Induced Mice of Indian Gooseberry and Barley Sprout Complex To confirm the effect on the organ and fat tissue weight change of obesity-induced mice from high fat diet of the complex of the Indian gooseberry extract and barley sprout extract prepared by the preparation method suggested in the experimental method, organ (liver, kidney, spleen) and white fat tissue (subcutaneous fat, visceral fat (epididymal fat and intraperitoneal fat)) of the experimental animals were measured. As suggested in Table 10, the total amount of the white fat tissue and the weight of the subcutaneous fat tissue and visceral fat tissue of the control group in which obesity was induced by high fat diet were 7.06±0.72, 3.57±0.62 and 3.49±0.32, respectively, and in the complex of Indian gooseberry and barley sprout, Example 3, compared to the control group, according to the administration group of 100, 200 and 400 mg/kg, the total amount of the white fat tissue was reduced to 5.52±0.86, 5.37±0.31 and 3.95±0.41, respectively, and the weight of the subcutaneous fat tissue was reduced to 2.62±0.43, 2.31±0.18 and 1.54±0.31, and the weight of the visceral fat tissue was reduced to 2.90±0.67, 3.06±0.14 and 2.41±0.15, and thereby it was confirmed that the complex of Indian gooseberry and barley sprout reduced the weight of fat tissue in the concentration dependent way, and it was confirmed that the complex of the Indian gooseberry extract and barley sprout extract showed an excellent effect on inhibition of body fat accumulation.

Figure 10:
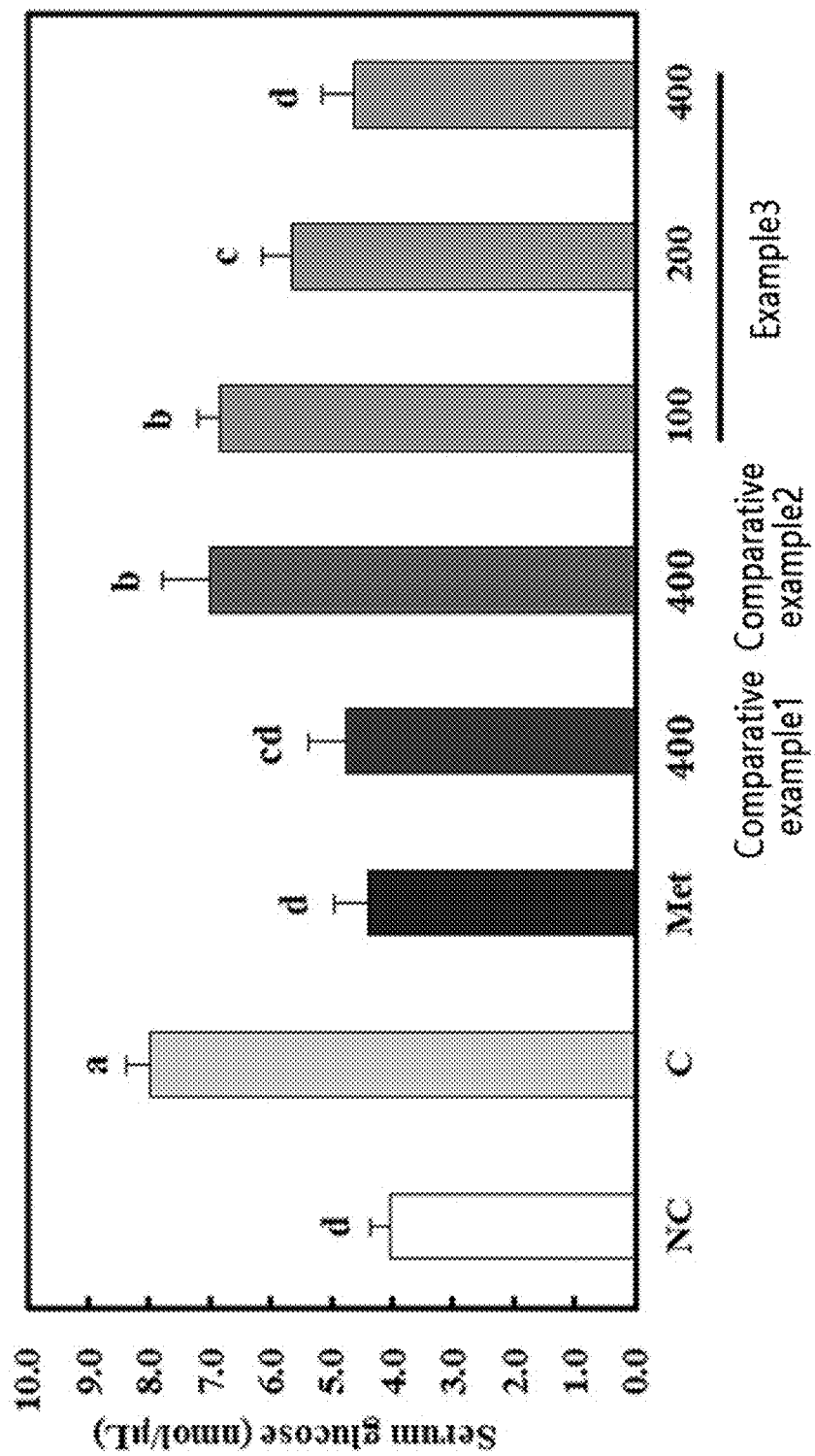
FIG. 10 is a drawing which shows the blood sugar (glucose) from experimental animals of the complex of Indian gooseberry extract and barley sprout extract, compared when treated as a single substance.

3-12. Confirmation of Effect on Blood Sugar Change of Obesity-Induced Mice of Indian Gooseberry and Barley Sprout Complex To confirm the effect on the blood sugar change of obesity-induced mice from high fat diet of the complex of the Indian gooseberry extract and barley sprout extract prepared by the preparation method suggested in the experimental method, the blood sugar of the experimental animals was measured. As suggested in FIG. 10, the single substance of Indian gooseberry and barley sprout showed the blood sugar numerical value of 4.74±0.64 and 6.99±0.79, respectively, at the same concentration of 400 mg/kg, and in the complex of Indian gooseberry and barley sprout, Example 3, the blood sugar was 4.63±0.51, and a significant reduction effect was shown compared to the single substance. In addition, in the treatment group of 100, 200 and 400 mg/kg, it was confirmed that the complex of Indian gooseberry and barley sprout reduced blood sugar in the concentration dependent way, and thereby it was confirmed that the complex of the Indian gooseberry extract and barley sprout extract showed an excellent effect on blood sugar reduction.

Figure 11:
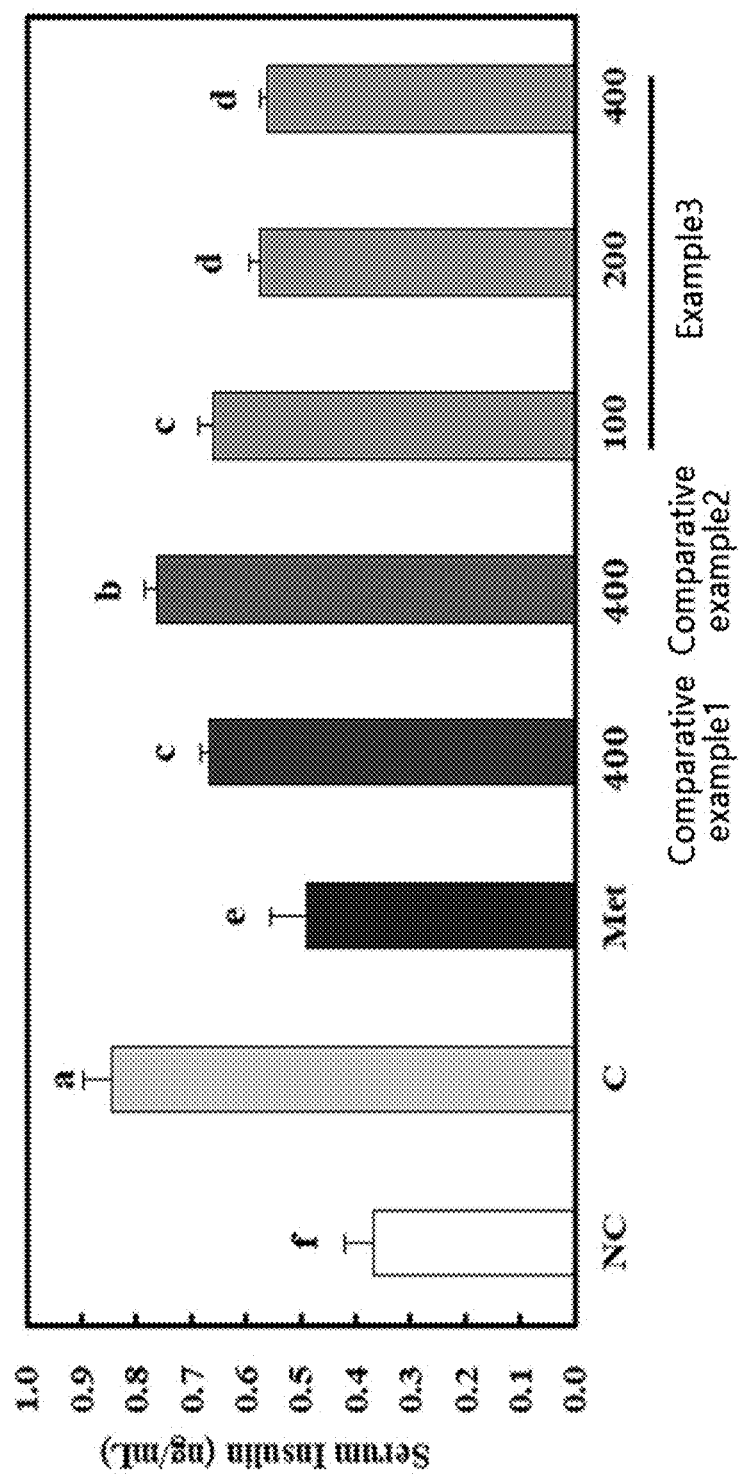
FIG. 11 is a drawing which shows the insulin in blood from experimental animals of the complex of Indian gooseberry extract and barley sprout extract, compared when treated as a single substance.

3-13. Confirmation of Effect on Insulin Change in Blood of Obesity-Induced Mice of Indian Gooseberry and Barley Sprout Complex To confirm the insulin change of obesity-induced mice from high fat diet of the complex of the Indian gooseberry extract and barley sprout extract prepared by the preparation method suggested in the experimental method, the insulin in blood of the experimental animals was measured. As suggested in FIG. 11, the single substance of Indian gooseberry and barley sprout showed the insulin numerical value in blood of 0.67±0.01 and 0.76±0.02, respectively, at the same concentration of 400 mg/kg, and in the complex of Indian gooseberry and barley sprout, Example 3, the insulin in blood was 0.56±0.01, and a significant reduction effect was shown compared to the single substance. In addition, in the treatment group of 100, 200 and 400 mg/kg, it was confirmed that the complex of Indian gooseberry and barley sprout reduced insulin in the concentration dependent way, and thereby it was confirmed that the complex of the Indian gooseberry extract and barley sprout extract showed an excellent effect on reduction of insulin in blood.

TABLE 10

| Groups | NC | C | Met | HFD supplementation | | |
|---|---|---|---|---|---|---|
| | | | | Example3 100 | Example3 200 | Example3 400 |
| Initial body weight (g) | 19.11 ± 0.23$^{ra}$ | 19.35 ± 0.84 | 19.26 ± 0.66 | 19.40 ± 0.72 | 19.57 ± 0.40 | 18.82 ± 0.53 |
| Final body weight (g) | 32.24 ± 3.74$^a$ | 50.27 ± 3.67$^a$ | 39.46 ± 2.16$^d$ | 47.53 ± 3.56$^{ab}$ | 45.35 ± 3.30$^{bc}$ | 43.52 ± 2.16$^c$ |
| Weight gain (g)* | 13.13 ± 3.67$^d$ | 30.92 ± 3.53$^a$ | 20.20 ± 1.89$^c$ | 28.13 ± 3.93$^{ab}$ | 25.78 ± 3.35$^b$ | 24.70 ± 1.85$^b$ |
| Food intake (g/day/mouse) | 2.49 ± 0.19$^c$ | 2.91 ± 0.23$^a$ | 2.66 ± 0.18$^b$ | 2.89 ± 0.18$^a$ | 2.98 ± 0.21$^a$ | 2.71 ± 0.20$^b$ |
| FER** | | 5.03 ± 1.41$^d$ | 10.12 ± 1.15$^a$ | 7.25 ± 0.68$^c$ | 9.28 ± 1.30$^{ab}$ | 8.25 ± 1.07$^{bc}$ | 8.68 ± 0.65$^b$ |

Figure 12:
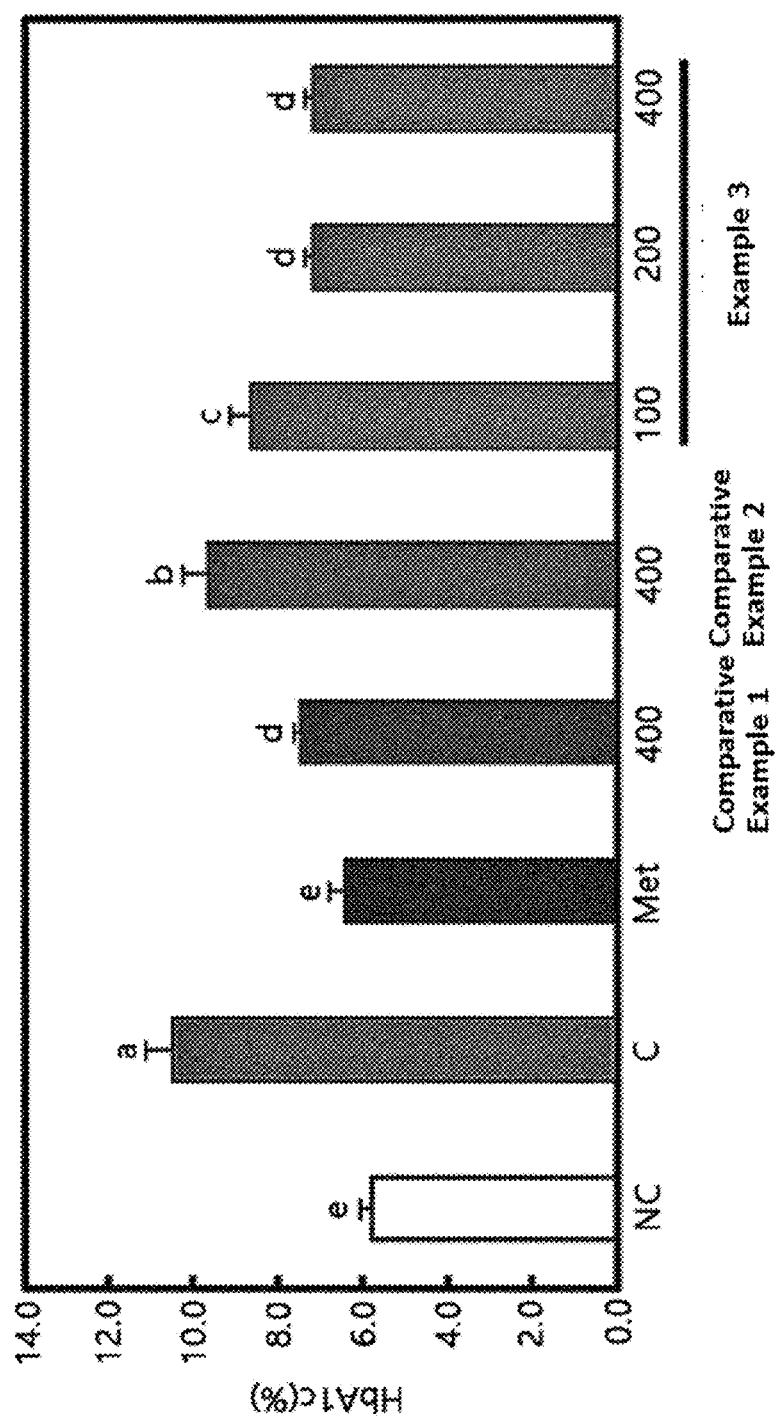
FIG. 12 is a drawing which shows the glycated hemoglobin (Hemoglobin A1c; HbA1c) in blood from experimental animals of the complex of Indian gooseberry extract and barley sprout extract, compared when treated as a single substance.

3-14. Confirmation of Effect on Glycated Hemoglobin (HbA1c) in Blood of Obesity-Induced Mice of Indian Gooseberry and Barley Sprout Complex To confirm the change of glycated hemoglobin in blood of obesity-induced mice from high fat diet of the complex of the Indian gooseberry extract and barley sprout extract prepared by the preparation method suggested in the experimental method, the HbA1c in blood of the experimental animals was measured. As suggested in FIG. 12, the single substance of Indian gooseberry and barley sprout showed the HbA1c in blood of 7.50±0.11 and 9.67±0.57, respectively, at the same concentration of 400 mg/kg, and in the complex of Indian gooseberry and barley sprout, Example 3, the insulin in blood was 7.15±0.22, and a significant reduction effect was shown compared to the single substance. In addition, in the treatment group of 100, 200 and 400 mg/kg, it was confirmed that the complex of Indian gooseberry and barley sprout reduced HbA1c in blood in the concentration dependent way, and thereby it was confirmed that the complex of the Indian gooseberry extract and barley sprout extract showed an excellent effect on reduction of HbA1c in blood.

What is claimed is:

1. A method for prevention, improvement or treatment of metabolic syndrome, comprising:
    administering a complex of Indian gooseberry (*Emblica officinalis*) extract and barley sprout (*Hordeum vulgare*) extract as an active ingredient to a subject in need thereof,
    wherein the weight ratio of Indian gooseberry extract to barley sprout extract is 4:1 to 1:1,
    wherein the metabolic syndrome is obesity,
    wherein the Indian gooseberry extract comprises 1 to 5 mg/g of ellagic acid under the condition of acid hydrolysis, or 5 to 25 mg/g of free ellagic acid under the condition of no acid hydrolysis, and
    wherein the barley sprout extract comprises 6 to 11 mg/g of saponarin.

2. The method according to claim 1, wherein the complex of Indian gooseberry extract and barley sprout extract retains the efficacy of fat accumulation inhibition and weight loss, by inhibiting fat digestion, absorption and synthesis, by promoting lipolysis, or by inhibiting the enzymatic activity of pancreatic lipase; or retains the efficacy of reduction of blood sugar, insulin and glycated hemoglobin, by regulating absorption of blood sugar and promoting glucose metabolism.

3. The method according to claim 1, wherein the metabolic syndrome further comprises diabetes.

4. The method according to claim 1, wherein the method comprises administering to a subject in need thereof an Indian gooseberry extract or barley sprout extract obtained by squeezing or extracting using an extraction solvent selected from the group consisting of water, lower alcohols of 1 to 4 carbon atoms and mixtures thereof.

5. The method according to claim 1, wherein the Indian gooseberry extract or barley sprout extract is in a form of dry powder.

6. The method according to claim 1, wherein the complex of Indian gooseberry (*Emblica officinalis*) extract and barley sprout (*Hordeum vulgare*) extract is comprised in a pharmaceutical composition, and is administered to the subject in need thereof by administering the pharmaceutical composition.

7. The method according to claim 1, wherein the complex of Indian gooseberry (*Emblica officinalis*) extract and barley sprout (*Hordeum vulgare*) extract is comprised in a food composition, and is administered to the subject in need thereof by administering the food composition.

* * * * *